US012691219B2

(12) United States Patent
West

(10) Patent No.: US 12,691,219 B2
(45) Date of Patent: Jul. 28, 2026

(54) FLOW METERING INSERT AND/OR DEVICE

(71) Applicant: Jonathan Charles Devlin West, Chesham (GB)

(72) Inventor: Jonathan Charles Devlin West, Chesham (GB)

( * ) Notice: Subject to any disclaimer, the term of this patent is extended or adjusted under 35 U.S.C. 154(b) by 1200 days.

(21) Appl. No.: 17/618,379

(22) PCT Filed: Jun. 18, 2020

(86) PCT No.: PCT/GB2020/051480
§ 371 (c)(1),
(2) Date: Dec. 10, 2021

(87) PCT Pub. No.: WO2020/254814
PCT Pub. Date: Dec. 24, 2020

(65) Prior Publication Data
US 2022/0305199 A1      Sep. 29, 2022

(30) Foreign Application Priority Data
Jun. 18, 2019     (GB) ...................................... 1908744

(51) Int. Cl.
*A61M 5/168*       (2006.01)
*A61M 5/14*       (2006.01)
(Continued)

(52) U.S. Cl.
CPC ...... *A61M 5/16886* (2013.01); *A61M 5/1411* (2013.01); *A61M 5/1413* (2013.01); *A61M 5/165* (2013.01); *A61M 2205/3334* (2013.01)

(58) Field of Classification Search
CPC .... A61M 5/14; A61M 5/1411; A61M 5/1413; A61M 5/162; A61M 5/165;
(Continued)

(56) References Cited

U.S. PATENT DOCUMENTS 2,479,786 A      8/1949  Stevens
4,136,692 A  *   1/1979  Goldowsky .......... A61M 5/1411
137/551
(Continued)

FOREIGN PATENT DOCUMENTS

CN       1434731 A      8/2003
CN    107530492 A      1/2018
(Continued)

OTHER PUBLICATIONS

First Office Action issued in Chinese Patent Application Serial No. 202080055329.1 on Sep. 5, 2023.
(Continued)

*Primary Examiner* — Michael J Tsai
*Assistant Examiner* — Anthony Christopher Misistia
(74) *Attorney, Agent, or Firm* — Brian J. Colandreo; Jeffrey T. Placker; Holland & Knight LLP

(57)              ABSTRACT

A flow metering insert (10) for a drip chamber (50) is provided that is suitable for use in intravenous administration. The insert comprises: a primary liquid flow channel with an inlet, an outlet, and a flow-resistant passage between the inlet and the outlet; and a flow indicating channel in communication with the primary liquid flow channel between the inlet and the flow-resistant passage. The flow-resistant passage provides a resistance to liquid flow such that liquid is forced into the flow indicating channel and reaches a height proportional to the rate of liquid flow through the primary liquid flow channel. The flow-resistant passage and the flow indicating channel are at least partially defined by one or more first recesses and/or channels in the insert such that the flow-resistant passage and the flow indicating channel are formed between the insert and a wall of the drip chamber when the insert is inserted into the drip chamber.

20 Claims, 12 Drawing Sheets

(51) Int. Cl.
    *A61M 5/165*        (2006.01)
    *G01F 1/52*         (2006.01)

(58) Field of Classification Search
    CPC .......... A61M 5/16877; A61M 5/16886; A61M
            5/1689; A61M 2202/0007; A61M
            2205/3334; A61M 2205/3327; A61M
            2205/3379; G01F 1/37; G01F 1/375;
                             G01F 1/52
    See application file for complete search history.

(56)             References Cited

U.S. PATENT DOCUMENTS

| | | | |
|---|---|---|---|
| 4,291,693 | A | 9/1981 | Todd et al. |
| 4,361,147 | A | 11/1982 | Aslanian et al. |
| 4,476,719 | A | 10/1984 | Millar et al. |
| 4,523,464 | A | 6/1985 | Pedersen et al. |
| 6,599,273 | B1 * | 7/2003 | Lopez ...................... F21K 2/00 |
| | | | 604/905 |
| 2006/0264850 | A1 * | 11/2006 | Mottola ............... A61M 5/1411 |
| | | | 604/254 |
| 2007/0151366 | A1 | 7/2007 | Mcdonald et al. |
| 2012/0179117 | A1 * | 7/2012 | Wang .................. A61M 1/0281 |
| | | | 604/256 |

FOREIGN PATENT DOCUMENTS

| | | |
|---|---|---|
| CN | 108334136 A | 7/2018 |
| EP | 2949352 A1 | 12/2015 |
| EP | 3294379 B1 | 4/2019 |
| WO | 2005/119181 A1 | 12/2005 |
| WO | 2020/254814 A1 | 12/2020 |

OTHER PUBLICATIONS

International Search Report and Written Opinion issued on Aug. 7, 2020 in related International Application No. PCT/GB2020/051480. Search Report issued in the related Application Serial No. GB1908744.4 on Dec. 17, 2019.

\* cited by examiner

10p $\theta_v$

10r

50w

Figure 4c $\theta_v$

FLOW METERING INSERT AND/OR DEVICE

CROSS-REFERENECE TO RELATED APPLICATIONS

This application is a U.S. National Stage of International Patent Application No. PCT/GB2020/051480, filed 18 Jun. 2020, which claims priority to Great Britain Patent Application No: 1908744.4, filed on 18 Jun. 2019. The disclosures of which are incorporated herein by reference in their entirety.

TECHNICAL FIELD

This invention relates generally to flow meter devices and/or parts thereof suitable for the administration of intravenous solutions. Particularly, but not exclusively, the invention relates to a flow metering insert for a drip chamber used in intravenous administration, a flow meter device comprising the insert, and an intravenous administration set comprising the insert.

BACKGROUND TO THE INVENTION

Intravenous (IV) administration systems are generally used to infuse various types of parenteral solutions into a patient. An IV administration system provides a means of controlling the sterile passage of a liquid (e.g. saline, glucose solution, etc.) from a rigid or flexible supply container, such as an IV bag, into a patient. Conventional IV administration systems feature a closed chamber with a nozzle outlet (a so-called drip chamber), creating drops when the liquid flows. The purpose of the drip chamber is to enable the liquid flow rate to be calculated by counting the number of drops per unit time. This can be time consuming and inaccurate, as drop size is not constant, and the conversion of drop timing to liquid flow rate can be difficult. A number of well-established flow meter designs have been adapted for use in IV liquid administration.

Variations on the well-known rotameter design (e.g. U.S. Pat. No. 3,587,313A) employ a small ball of proper specific gravity (usually greater than the liquid, though it may also be a float in some designs) positioned within a vertically arranged tapered indicating chamber (or tube), with the liquid inlet at the lower smaller end of the chamber. The ball is pushed towards the larger cross sectional area of the indicating chamber as the liquid flows around the ball, such that the position of the ball is indicative of the liquid flow rate. Though these devices enable more accurate regulation and adjustment of flow rate, they are expensive to manufacture due to the high tolerances required, as well as the potentially complex assembly of components.

Another type of flow meter device is of the reverse flow type, such as that disclosed in U.S. Pat. No. 2,479,786A. The device in U.S. Pat. No. 2,479,786A employs a vertically arranged tube having a liquid inlet at the top and a short portion at the lower end bent back upon itself to form an upwardly extending portion (indicating chamber/tube) with an opening at its upper end. This arrangement is enclosed within a larger sealed housing (i.e. drip chamber) having an outlet to further tubing leading to the patient. A small orifice in the wall of the tube at the bend allows liquid to flow downwards from the inlet into the drip chamber. Liquid flow, combined with the resistance to flow caused by the orifice, causes the liquid level in the upward portion to rise to a level proportional to the flow rate and thus serve as an indicating chamber/tube. This design is simpler than the rotameter variants, but is inaccurate at low flow rates, and it is difficult to manufacture multiple units with consistent geometry, further affecting calibration and accuracy.

The device in U.S. Pat. No. 4,136,692A uses a similar principle to that in U.S. Pat. No. 2,479,786A, replacing the bent tube with two chambers/tubes (an inlet chamber and an indicating chamber) interconnected at their lower ends and enclosed within a larger sealed housing (the drip chamber) with an outlet to the patient. The small orifice in U.S. Pat. No. 2,479,786A is replaced with highly accurate orifice disks of minimal thickness (approximately 0.001 in or 0.0254 mm). This is intended to minimise any effects of changing temperature and viscosity on measurement accuracy, but the design remains a relatively complex assembly of small parts, resulting in higher manufacturing costs compared to standard IV administration systems.

Another variation of the reverse flow design is disclosed in U.S. Pat. No. 4,291,693A, in which the orifice disc of U.S. Pat. No. 4,136,692A is replaced with a flow restrictor tube, wherein at least a portion of the flow restrictor tube is oriented such that the liquid passing through it moves upwardly to help avoid trapping any air bubbles. Similar to U.S. Pat. Nos. 4,136,692A and 2,479,786A, the resistance to flow caused by the flow restrictor tube causes the liquid level in the upwardly directed indicating tube to rise to a level proportional to the flow rate. However, like the device in U.S. Pat. No. 4,136,692A, the design remains relative complex, resulting in higher manufacturing costs.

U.S. Pat. No. 4,523,464A discloses another variation of the reverse flow type device which can be fabricated from thermoplastic materials. In particular, the device comprises a flow restricting orifice at the lower end of the vertical inlet tube and indicating chamber, but the walls of the inlet tube and/or the indicating chamber are formed by a wall of the enclosing housing. The device is relatively simple to fabricate compared to U.S. Pat. Nos. 4,136,692A and 4,291, 693A, however, still requires assembly and welding of multiple component parts. In addition, it is not well suited to sudden changes in flow rate and is designed for measuring liquid flow through a partially-full pipe such that the inlet tube is fed by gravity.

A further variation on the reverse flow type device is disclosed in the applicant's prior patent EP3294379B1, in which the flow meter device is formed from two separately moulded parts that can be simply assembled by fitting one inside the other. A first part comprises the drip chamber, a second part comprises the inlet tube, and a substantially U-shaped flow restrictor passage and an indicating chamber are formed between the first and second parts when assembled. Although simple to manufacture and assemble it still requires the moulding of two bespoke parts.

An aim of the present invention is to provide an improved flow meter device that is simpler to fabricate and assemble and more reliable than previous reverse flow type designs, yet is still comparable in cost, and easier, quicker, and more accurate to use than the standard IV administration systems based on drop counting.

Aspects and embodiments of the present invention have been devised with the foregoing in mind.

SUMMARY OF THE INVENTION

According to a first aspect of the invention, there is provided a flow metering insert that can be used with a drip chamber, e.g. for use in intravenous (IV) liquid administration. The insert may comprise a primary liquid flow channel and a flow indicating channel. The primary liquid flow channel may comprise an inlet passage, an outlet, and a flow-resistant passage between the inlet passage and the outlet. The inlet passage may be connectable to a liquid source, such as a liquid container or IV bag, for receiving a liquid flow. The flow indicating channel may be in communication with the primary liquid flow channel between the inlet passage and the flow-resistant passage. The flow-resistant passage provides a resistance to a liquid flow therethrough such that liquid is forced into the flow indicating channel and reaches a level or height proportional to the rate of liquid flow through the primary liquid flow channel, inlet passage, and/or flow-resistant passage.

The insert can be used with and inserted into a standard sized and unmodified transparent drip chamber known in the art, e.g. of a drip set or infusion set used in medicine and/or intravenous (IV) administration, to form a flow meter device. Such a drip chamber typically has smooth internal surfaces. In particular, the insert can be inserted into the upper portion of a standard drip chamber, e.g. through an opening in its top end. The drip chamber may be substantially rigid or flexible. The liquid level or height in the flow indicating channel can therefore be viewed through the sidewall/external wall of the drip chamber. A cover or lid with a means for connecting the flow meter device to a liquid source (e.g. an IV bag or container), such as a standard vented or non-vented spike as is known in the art, can be attached to the drip chamber to close and seal the drip chamber and define a passage for liquid flow from the liquid source to the inlet passage of the insert. In some drip chambers, the cover or lid may be integral with the drip chamber, For example, in a two-part drip chamber comprising an upper portion (e.g. having the spike) and a lower portion that are attachable to each other to close and seal the drip chamber, the insert can be inserted into the upper part through an opening in its lower end. Standard tubing, accessories and/or flow controllers can be used downstream from the resulting flow meter device. When inserted into said drip chamber and connected to a liquid source, the flow indicating channel of the insert provides a visual indication of the liquid flow rate, which is more direct, accurate and reliable than methods based on counting drops in an otherwise standard drip chamber without such an insert. The insert can therefore be retrofitted to existing standard IV administration systems to provide improved flow metering at minimal cost and/or disruption to standard IV administration set manufacturing practices. Further, the outlet of the insert may comprise a drip forming orifice, such that a flow of drops from the outlet may still be visible in the lower portion of the drip chamber as liquid exits the insert, in accordance with ISO-8536-4 (an international standard that mandates drops must be continuously visible in gravity-fed infusion equipment for medical use). The resulting flow meter device can be "primed" in the same manner as existing drip sets, which involves squeezing and releasing a flexible lower portion of the drip chamber (below the insert) to draw liquid down through the primary liquid passage from the liquid source and expel air upwards into the liquid source.

The primary liquid flow channel and/or flow indicating channel may be at least partially defined by the insert. The primary liquid flow channel and/or flow indicating channel may be partially defined by the insert, such that and the primary liquid flow channel and/or the flow indicating channel are completed/fully defined when the insert is inserted into the drip chamber. Alternatively, the primary liquid flow channel and/or flow indicating channel may be fully defined by or in the insert.

The inlet passage may be or comprise a closed channel. The flow-resistant passage and/or the flow indicating channel may be at least partially defined by the insert. The insert may comprise one or more recesses and/or channels configured to at least partially define the flow-resistant passage and the flow indicating channel. The one or more recesses and/or channels may be one or more first recesses and/or first channels (as opposed to a second recess or second channel, as is defined later). The flow-resistant passage and/or the flow indicating channel may be at least partially defined by the one or more recesses and/or channels in the insert such that, when inserted into the drip chamber, the flow-resistant passage and/or the flow indicating channel is formed or located between the insert and (an interior surface of) a wall (e.g. a sidewall or external wall) of the drip chamber.

Where the flow-resistant passage and/or the flow indicating channel is/are partially defined by the insert, the flow-resistant passage and/or the flow indicating channel may be or comprise one or more recesses or open channels formed in a surface of the insert. The one or more recesses or open channels may be closed, scaled and/or completed by (an interior surface of) a wall (e.g. a sidewall or external wall) of the drip chamber when the insert is inserted into the drip chamber. This may greatly simplify manufacture and thereby reduce the cost of manufacturing the insert. For example, it can be manufactured within standard injection moulding tolerances and used with standard drip chambers widely available and used in the art.

The surface may be a mating surface and/or an outer surface (i.e. facing substantially away from the insert) of the insert. The mating surface may be configured to mate with, i.e. contact/abut and/or seal against, the interior surface of a wall (e.g. sidewall or external wall) of the drip chamber when the insert is inserted into the drip chamber. The mating surface may be configured to conform to and/or contact an interior surface of a wall (e.g. sidewall or external wall) of the drip chamber when the insert is inserted into the drip chamber. The mating surface may be substantially smooth. Alternatively or additionally, the mating surface may be or comprise one or more sealing ribs that extend around the one or more recesses or open channels that partially define the flow-resistant passage and/or the flow indicating channel. The mating surface and/or the one or more sealing ribs may be configured to at least partially deform the interior surface of the wall, and/or be at least partially deformed by the interior surface of the wall, to make a liquid-tight seal therebetween.

Where the flow-resistant channel and/or the flow indicating channel is/are fully defined by the insert, the flow-resistant passage and/or the flow indicating channel may be or comprise one or more closed channels, e.g. defined by the one or more recesses and/or channels. Such an insert would not rely on the geometry of the drip chamber to function (since the flow-resistant channel and/or the flow indicating channel are internal passages/channels of the insert), and could therefore be used with arbitrarily shaped drip chambers, provided the insert can fit into it. Alternatively, the insert may itself form a stand-alone flow meter device, without a needing to be inserted into a drip chamber. For example, where the formation and viewing of drips from the outlet is not required, the insert may be connected in-line with a liquid circuit to monitor and/or set a flow rate therethrough.

A liquid "channel" may mean a closed channel, an open channel, or a channel with one or more open and closed channel portions in the insert. A closed channel means a channel with one or more channel walls that enclose a liquid flow therethrough. An open channel means a channel with at least a portion of a channel wall open and exposed to its immediate surroundings such that a liquid flow therethrough is not fully enclosed (e.g. it can be formed by a recess).

The insert may be configured, shaped and/or dimensioned to provide an interference fit within the drip chamber. In particular, the insert may be configured shaped and/or dimensioned to provide an interference fit between the mating surface and the wall of the drip chamber. The interference fit may provide a liquid-tight seal between the mating surface and the wall of the drip chamber, to close and seal the one or more recesses or open channels and fully define or complete the flow-resistant passage and/or the flow indicating channel. Thus, additional sealing and/or bonding of the insert to the interior surface of the drip chamber wall is not required to provide a liquid-tight seal, which simplifies assembly of the resulting flow meter device.

The insert may be formed of or comprise a substantially rigid material. In this case, the insert may provide an interference fit within a substantially flexible/deformable portion of the drip chamber to provide a liquid-tight seal therebetween. Alternatively, the insert may be formed of or comprise a substantially flexible, deformable and/or compressible material. In this case, the insert may provide an interference fit within a substantially rigid portion of the drip chamber to provide a liquid-tight seal therebetween. Where the insert is formed of or comprises a substantially rigid material, the wall of the drip chamber may be substantially flexible or less rigid than the insert, such that interior surface of the wall at least partially flexes or deforms to conform to the mating surface of the insert when the insert is inserted into the drip chamber. Alternatively, where the insert is formed of or comprises a substantially deformable material, the wall of the drip chamber may be substantially rigid, such that the mating surface of the insert at least partially deforms to conform to the interior surface of the sidewall. In either case, the mating surface is configured such that it can conform (after deforming or not deforming) to the final interior surface of the wall when the insert is inserted into the drip chamber.

The insert may be formed from or comprise a thermoformable material, such as a plastic and/or thermoplastic material. Example materials include but are not limited to: acrylonitrile butadiene styrene (ABS) or equivalent, polyvinyl chloride (PVC) or PVC-free equivalent, polyethylene, polycarbonate, nylon, polypropylene, polyurethane, ethylene vinyl acetate, or any plastic permitted for use in intravenous applications. ABS or equivalent may be suitable for forming a substantially rigid insert. PVC or PVC-free equivalent may be suitable for forming a substantially flexible, deformable and/or compressible insert.

A flow meter device comprising the insert may be configured to be arranged substantially vertically in use, such that liquid can flow downwards through the inlet passage under gravity. References to "upper" and "lower" below refer to this orientation.

The insert may have a length and a width. The length may be in a longitudinal (vertical) direction/axis. The length may be in an insertion direction, the insertion direction corresponding to the direction in which the insert is inserted into the drip chamber during assembly. The width may be in a transverse direction.

Although described above in the context of IV administration, the insert may also be used with, e.g. in series with other flow devices, such as electronic pumps to monitor and/or set a flow rate. As such, more generally, the insert may be used with and inserted into a liquid flow chamber or housing comprising an opening for receiving the insert and an outlet for receiving a liquid flow from the outlet of the insert. The outlet may be arranged downstream of the insert outlet. A flow meter device may be formed by the insert and the flow chamber or housing. The insert may be configured to close and/or seal the flow chamber or housing. The insert may be configured to close and/or seal the opening of the flow chamber or housing. Alternatively, a cover or lid with a means for connecting the device to a liquid source may be used to close and seal the opening of the flow chamber or housing. Tubing, flow accessories and/or flow controllers can be connected to/used downstream from the outlet of the flow chamber or housing. The flow chamber or housing may comprise one or more walls (e.g. sidewalls or external walls) that define an internal volume, cavity or space sized to accommodate the insert. The wall(s) may extend from the opening in the insertion direction. At least a portion of the wall(s) of the flow chamber or housing may be substantially transparent such that the liquid level or height in the flow indicating channel can be viewed through the wall. The internal volume, cavity or space of the flow chamber or housing may have a substantially circular horizontal cross-section (e.g. the interior of the drip chamber may be substantially cylindrical), or have a non-circular and/or arbitrary horizontal cross-section. The interior surface of the wall(s) may be tapered (inwardly) or non-tapered in the insertion direction. The flow chamber or housing may be substantially tubular. The flow chamber or housing may be or comprise a tube or tubular member. The flow chamber may be or comprise a container or bag having an opening, portion, and/or tubular portion, configured to receive and/or accommodate the insert, such that the insert can provide a visual indication of flow rate into and/or through the container/bag/chamber. The exterior of the flow chamber or housing may have a regular or irregular shape. For example, the insert may be used for placing in a catheter bag to monitor rate of urine output. In other words, the insert geometry can be configured to fit many different flow chamber geometries and is not limited by application.

Alternatively, where the flow-resistant passage and/or the flow indicating channel is partially defined by the insert, a collar or ring may be used to close and/or seal the one or more recesses or open channels. The collar or ring may extend at least partially around the insert and at least partially the length of the insert. For example, when the insert is inserted into the collar or ring, or the collar or ring is positioned at least partially around the insert, the flow-resistant passage and/or the flow indicating channel may be formed between the insert and (an interior surface of) a wall (e.g. sidewall) of the collar or ring, e.g. as described above. A flow meter device may be formed by the insert and the collar/ring alone, or the insert and collar/ring may be inserted into a drip chamber or flow chamber to form the flow meter device (in the latter case, the wall of the drip/flow chamber does not close and seal the one or more recesses or open channels. Tubing, flow accessories and/or flow controllers can be connected to/used downstream from the outlet of the insert.

The inlet passage of the insert may have an inlet end (upper end) and an outlet end (lower end). The upper end of the inlet passage may comprise an opening for receiving a liquid flow.

The lower end (outlet end) of the inlet passage may be in communication with the one or more recesses or open channels in the external/mating surface of the insert that partially define the flow resistant passage and/or the flow indicating channel. The outlet of the insert may be in communication with (an outlet end) of the flow-resistant passage.

The flow indicating channel may comprise an inlet end in communication with an outlet end of the inlet passage and an inlet end of the flow-resistant passage. The flow indicating channel may extend substantially upwardly from its inlet end (lower end) to an open outlet end (upper end) when the insert is arranged substantially vertically.

The operation/use of the insert relies on the principle that a liquid level/height in the flow indicating channel is proportional to the liquid flow rate through the flow-resistant passage. The change in liquid level/height with flow rate is determined by the resistance to flow provided by the flow-resistant passage. For example, for a given flow rate, a higher resistance to flow results in a higher liquid level/height in the flow indicating channel. The flow indicating channel may include a graduated scale to provide a visual measure of the liquid level or height in the flow indicating channel and thereby the rate of liquid flow through the flow-resistant passage (and/or the inlet passage and/or primary liquid flow channel). The scale includes graduations or indices spaced at given intervals corresponding to given flow rate intervals. A visible float may be provided to facilitate reading of the liquid level/height.

At high flow rates, the liquid level/height may exceed the height of the flow indicating channel. The open outlet end of the flow indicating channel may provide an overflow to allow liquid to continue to flow freely through the resulting flow meter device under high flow conditions (e.g. greater than 250 ml/hour).

The flow indicating channel may be substantially straight, curved and/or comprise one or more bends. The flow indicating channel may extend substantially vertically from its inlet end when the insert is arranged vertically. Alternatively, at least a portion of the flow indicating channel may extend from its inlet end at an angle (a non-zero angle) to vertical when the insert is arranged substantially vertically (or at an angle to the longitudinal axis of the insert). The angle may be in the range of substantially 5-85 degrees from vertical (or the longitudinal axis), or 10-80, or 15-75, or 20-70, or 25-65, or 30-60, or 35-55 degrees, or any combination or sub-range thereof. Angling at least a portion of the flow indicating channel means that the vertical component of the scale is represented on an angle. This spreads the vertical components of the scale over a larger distance (i.e. increasing the absolute spacing/separation between given graduations/increments) which may make the liquid level/height easier to measure/read and/or provide room for additional sub-graduations thus increasing the resolution of the scale. This may be particularly useful at or near the inlet end of the flow indicating channel where the liquid level/height corresponds to low flow rates (e.g. below 50 ml/hour). The flow indicating channel may be curved about the longitudinal axis of the insert and/or about a transverse axis of the insert. For example, the flow indicating channel may curve away from the longitudinal axis, e.g. when viewed from the side of the insert. Where the interior surface of the wall of the drip chamber is curved (i.e. about the longitudinal axis of the insert), an angled flow indicating channel may also be curved (i.e. about the longitudinal axis of the insert), e.g. it may be substantially helical in shape. An angled and/or curved flow indicating channel may allow the length of the insert to be reduced, e.g. to fit a flow/drip chamber with reduced size.

The flow indicating channel may comprise a first portion and a second portion arranged at different angles. The first portion may be a lower portion that extends from the inlet end of the flow indicating channel at an angle to vertical (or the longitudinal axis) when the insert is arranged substantially vertically, as described above. The second portion may be an upper portion that extends substantially vertically from the first portion when the insert is arranged substantially vertically. Alternatively, the second portion may extend from the first portion at an angle to vertical (or the longitudinal axis), wherein the angle is smaller (i.e. closer to vertical or the longitudinal axis) than the angle of the first/lower portion.

The change in liquid level or height in the flow indicating channel with flow rate changes may be dependent on the geometry and/or volume of the flow indicating channel. The lower the volume, the quicker the rate of change, and/or responsiveness of the level/height to changes in flow rate, and vice versa.

Alternatively or additionally, one or more notches or openings may be formed in a wall of the flow indicating channel configured to permit a liquid flow out of the flow indicating channel. As the liquid level in the flow indicating channel reaches the position of the notch and/or rises above the notch, some of the liquid can escape (into the drip chamber) via the notch. This means that much higher flow rates are needed for the liquid level in the flow indicating channel to continue to rise above the position of the notch, because the level rise must also overcome fluid loss via the notch. This provides for a non-uniform scale, with more flow sensitivity below the notch, and less flow sensitivity above it. Where there is more than one notch, each notch may be positioned at a different level in the flow indicating channel. Such a nonlinear scale may be desirable in instances where higher flow measurement accuracy is required at lower flow rates, but the same flow meter must also measure high flow rates. A linear scale in such instances may be impractically large.

The flow-resistant passage has a sufficient cross-section and/or length to provide the required flow resistance. The flow-resistant passage may have a uniform or non-uniform width/cross-section to flow. The flow-resistant passage may comprise an orifice. The use of an orifice restriction (rather than an elongate restriction, such as a narrow pipe/tube section) may make the assembled flow meter device less susceptible to changes in viscosity of the liquid. The more the resistance in the flow-resistant passage is provided by an orifice restriction, the less susceptible the flow rate measurement is to changes in liquid viscosity. The more the resistance is provided by a narrow pipe flow (e.g. in the case of an elongate restriction), the more susceptible it is to changes in liquid viscosity. As such, preferably the orifice is as short as possible in the direction of flow (within the constraints of the manufacturing process). A wall of the recess or open channel partially defining the flow-resistant passage may comprise a projection pointing or extending inwards, into the passage, or towards the centre of the passage to narrow the width of the flow-resistant passage. The projection may extend from a floor of the recess and oppose the wall of the drip chamber. Additionally or alternatively, the projection may extend from a sidewall of the recess or flow-resistant passage towards an opposing sidewall of the recess or flow-resistant passage. The orifice may be formed by a single projection, e.g. the projection may oppose a substantially straight portion of wall (e.g. a wall of the recess or the wall of the drip chamber), or the orifice may be formed by two opposing projections. The projection(s) may be substantially rectangular, V-shaped or triangular-shaped in cross-section. The more acute the angle θ, of the sidewalls forming the projection the more ideal the orifice becomes and the less susceptible the flow meter device is to changes in viscosity of the liquid. V-shaped projections are a compromise between performance and manufacturability.

The width of the orifice may provide sufficient resistance to liquid flow to result in a discernible change in liquid level/height in the flow indicating chamber when a flow rate through the flow resistant passage is between substantially 0-250 ml/hour. The width of the orifice may be in the range of substantially between 0.1-0.2 mm.

The change in liquid level/height in the flow indicating channel with flow rate through the flow-resistant passage is determined by the orifice dimensions. For example, for a given flow rate, a higher liquid level/height is achieved with narrower orifices. As such, the dimensions of the orifice may be chosen according to the application: based on the length, angle and/or height of the flow indicating channel; the desired range of flow rates measurable from the liquid level/height in the flow indicating channel; and/or the desired measurement resolution. For example, for a flow indicating channel with a given maximum height, the maximum measurable flow rate (before liquid overflows its upper end) is larger for wider orifices than it is for narrower orifices. However, a higher resolution scale (i.e. with indices/graduations at smaller flow rate intervals) can be used with narrower orifices. Similarly, where the flow indicating channel is angled, a wider orifice may be used, due to the spreading of the vertical components of the scale.

The flow-resistant passage may be shaped such that, when the insert is inserted into the drip chamber and arranged substantially vertically, liquid remains in the flow-resistant passage when liquid flow is stopped. The flow-resistant liquid passage may be substantially U-shaped when the insert is arranged substantially vertically. In this context, "U-shaped" means that the direction of liquid flow is substantially reversed on its passage through the flow-resistant passage (including V-shaped, C-shaped, etc.). As such, the flow-resistant passage includes a portion in which liquid flows substantially upwardly, when the insert is arranged substantially vertically. The flow-resistant passage may also comprise additional bends and/or curves.

The substantially U-shaped flow-resistant passage provides that, when liquid flow is stopped by the operator, the flow-resistant passage does not dry out and remains wet. This may prevent the build-up of solid deposits in the flow-resistant passage that may occur from evaporation of liquid, which may affect the cross-sectional area of the flow-resistant passage and thus the resistance to flow, introducing error to the measurement of liquid flow rate from the flow indicating channel.

Where the flow-resistant passage comprises an orifice, the orifice may be located at or near the lower portion of the U-shaped flow-resistant passage when the insert is arranged substantially vertically. This may ensure the orifice is submerged in use (preventing the orifice from drying out), and that drops do not form during the restricted part of the liquid flow. Avoiding drop formation may improve the reliability of the resulting flow meter device, since drops may not be consistent in volume or rate of formation.

The insert may be formed by a moulding process, such as injection moulding. In particular, the insert may be a single piece moulding. Optionally or preferably, the insert may be formed by a single direction injection moulding process. A single direction moulding process means that the mould creating the insert is made up of two parts, separated in a single direction (i.e. with no side cores or complex tooling required). In this way, the manufacture time and cost is reduced. Further, because the flow-resistant passage can be formed between the insert and (an interior surface of) a wall of the drip chamber, the critical geometry and dimensions of the flow-resistant passage (e.g. the orifice) may be achieved with regular injection moulding techniques and tolerances. For example, the inlet passage may be formed at an angle to vertical when the insert is arranged substantially vertically (or at an angle to the longitudinal axis), such that the outlet end of inlet passage extends to an outer surface of the insert and/or is in communication with the one or more recesses or open channels in the outer surface of the insert. Alternatively, the insert may be formed using a three-dimensional printing or a machining process.

Devices that rely on the same principle of a liquid level or height in an indicator column being proportional to flow through a flow-resistant passage have thus far been unreliable at low flow rates (below 50 ml/hour), and/or have required high tolerances and expensive manufacturing costs. The insert of the present invention allows improved accuracy and consistency of indicated flow, even at low flow rates, can be manufactured within standard injection moulding tolerances and used with standard drip chambers widely available and used in the art.

The insert may further comprise an exit chamber for directing a liquid flow from the flow-resistant passage to the outlet. The exit chamber may be in communication with an outlet end of the flow-resistant passage and the outlet. The exit chamber may comprise the outlet. The exit chamber may comprise an opening in a sidewall that is in communication with the outlet end of the flow-resistant passage. The sidewall opening and/or outlet end of the flow-resistant passage may be positioned at a level or height above the level/height of the outlet when the insert arranged vertically. The exit chamber may comprise a floor, base or bottom wall in which the outlet is located.

The exit chamber may comprise a channel extending from the sidewall opening and/or outlet end of the flow-resistant passage to direct and/or guide a liquid flow from the flow-resistant passage to the outlet without forming drops. The channel may be a second channel. The channel may be configured to draw liquid (e.g. substantially downwards) into the exit chamber by capillary action. The channel may be or comprise an open channel or recess formed at least partially in a sidewall of the exit chamber. The open channel may extend to the floor, base or bottom wall of the exit chamber.

The exit chamber may be at least partially defined by the insert. The exit chamber may be partially defined by the insert such that, when the insert is inserted into the drip chamber, the exit chamber is formed between the insert and a wall (e.g. a sidewall or external wall) of the drip chamber. The exit chamber may be formed by a recess in the insert. At least a portion of the recess may be closed by the wall (e.g. a sidewall or external wall) of the drip chamber when assembled. The wall of the drip chamber may form at least a portion of a sidewall of the exit chamber.

The exit chamber may further comprise an overflow opening positioned at a level or height between the level/height of the outlet and the level/height of the sidewall opening and/or outlet end of the flow-resistant passage. When inserted into the drip chamber, the overflow opening may be in communication with the lower portion of the drip chamber below the insert, such that liquid overflowing the exit chamber may drain to the lower portion of the drip chamber. This may prevent liquid filling up in the exit chamber which would otherwise introduce error to the measurement of flow rate, particularly the "zero line", from the flow indicating channel. The overflow opening may also allow air flow between the exit chamber and the low portion of the drip chamber. In addition, the exit chamber may comprise one or more vent openings located above the level/height of the overflow outlet and in communication with the interior of the drip chamber to permit air flow between the exit chamber and the rest of the drip chamber. In this way, the exit chamber may be an open chamber.

The insert may further be shaped and configured to provide a gap between insert and the wall of the drip chamber. The gap may extend the length of the insert. The gap may be provided a chamfered side of the insert, or a channel or recess. The overflow opening, gap, and/or vent opening(s) may prevent air locks in any/all non-liquid filled passages/channels/chambers and allow the resulting flow meter device to be "primed" in the same manner as existing drip sets, which involves squeezing and releasing a flexible portion of the drip chamber (the lower portion) to draw liquid down through the primary liquid flow passage from the liquid source and expel air upwards into the liquid source.

The insert may further comprise one or more lateral ribs, panels and/or projections extending from the insert towards the external wall of the drip chamber. The one or more lateral ribs and/or projections may be serve to encourage a tight interference fit inside the drip chamber and increase structural strength/rigidity of the insert, e.g. resistance to bending, flexing and/or twisting of the insert. The one or more lateral ribs and/or projections may extend in a substantially longitudinal and/or transverse direction. The lateral ribs or projections may comprise one or more openings or notches configured to avoid trapping air or liquid.

The insert may further comprise a filter element positioned upstream of the flow-resistant passage to prevent particles in the liquid being deposited in the flow-resistant passage which would otherwise adversely affect the reliability of the resulting flow meter device. The filter element may be positioned at or near the inlet end of the inlet passage. The filter element may be moulded to/into the inlet passage.

The insert may further comprise a vent channel or bubble vent channel in fluid communication with the lower/outlet end of the inlet passage configured for venting any bubbles in the liquid flow exiting the inlet passage before they reach the flow indicating channel. The vent channel may have a lower end in fluid communication with the lower/outlet end of the inlet passage and an open upper end. The lower end of the vent channel may be located upstream of the lower end of the flow indicating channel. The vent channel may run substantially parallel to and/or alongside the flow indicating channel. The vent channel may extend in a direction substantially parallel to the longitudinal axis of the insert. The vent channel may extend substantially vertically from its lower end when the insert is arranged substantially vertically. The vent channel is configured to allow any bubbles in the liquid flowing out of the inlet passage to rise upwards in the vent channel and not enter the flow indicating channel, which would otherwise adversely affect the flow measurement. The upper end of the vent channel may be at least the same height as the upper end of the flow indicating channel. This may prevent overspill/overflow of fluid (bubble and liquid) from the vent channel affecting any liquid levels higher than the upper end of the vent channel in the flow indicating channel.

According to a second aspect of the invention, there is provided a flow meter device comprising the insert of the first aspect and a flow chamber or housing for receiving the insert.

The flow chamber or housing may comprise an opening through which the insert can be inserted and an outlet for receiving a liquid flow from the outlet of the insert. The outlet of the flow chamber may be arranged downstream of the insert outlet for connecting to further components such as tubing, accessories and/or flow controllers downstream of the device. The flow chamber may comprise one or more walls (e.g. sidewalls or external walls). Features of the insert defined with reference to a wall of a drip chamber in the first aspect may equally be defined with reference to the wall(s) of the flow chamber. The wall(s) may define an internal volume, cavity or space sized to accommodate the insert. The wall(s) may extend from the opening in the insertion direction. At least one of the one or more walls may comprise a substantially transparent portion for viewing the liquid level/height in the flow indicating channel.

The internal volume, cavity or space of the flow viewing chamber may be substantially circular in cross-section (e.g. the interior of the flow chamber may be substantially cylindrical), or have a non-circular and/or arbitrary cross-section. The flow chamber or housing may be or comprise a tube or tubular member. The flow chamber may be or comprise a container or bag having an opening, portion, and/or tubular portion, configured to receive and/or accommodate the insert, such that the insert can provide a visual indication of flow rate into and/or through the container/bag/chamber. The interior surface of the wall(s) may be tapered (inwardly) or non-tapered in the insertion direction. The wall(s) of the drip chamber may be substantially rigid or flexible/deformable, or comprise a substantially rigid portion and a substantially flexible/deformable portion. The flow chamber or housing may be substantially tubular. The exterior of the flow chamber or housing may have a regular or irregular shape.

The flow chamber may be or comprise a drip chamber, such as a standard (at least partially) transparent drip chamber used in IV administration/drip sets known in the art. However, it will be appreciated that any flow chamber with suitable dimensions may be used, particularly for non-IV applications.

The flow chamber may have a length greater than the length of the insert. Where the flow chamber is a drip chamber for IV administration, it may have a length at least 40 mm greater than the length of the insert and the outlet of the insert may be positioned at least 5 mm from (an interior surface of) the wall of the drip chamber, to comply with ISO-8536-4.

The drip chamber may have a length of approximately 100 mm. The insert may have a length of approximately 60 mm. This may leave a usable reading scale of around 40 mm for the flow indicating channel.

The flow chamber may be a single part of comprise two or more separate portions that are attachable to each either. The opening for receiving the insert may be formed in an upper end of the flow chamber. The device may further comprise a cover or lid connectable to the flow chamber with a means for connecting the device to a liquid source (such as an IV bag or container). The cover or lid may be connectable to the opening of the flow chamber. The cover or lid may close and seal the flow chamber and define an inlet passage for liquid flow from the liquid source to the inlet passage of the insert. The cover or lid may comprise an inlet passage with an outlet end for connecting to the inlet passage of the insert and an inlet end for connecting to a liquid source.

Alternatively, the cover or lid may be integral with the flow chamber. The flow chamber may comprise the inlet passage with an outlet end for connecting to the inlet passage of the insert and an inlet end for connecting to a liquid source. In this case, the opening for receiving the insert may be a lower end of the flow chamber. The flow chamber may comprise a separate upper portion and lower portion that are attachable to each other. The upper portion may comprise the inlet passage. The lower portion may comprise the outlet. The opening for receiving the insert may be formed in the lower end of the upper portion.

An outlet end of the cover or lid's or flow chamber's inlet passage may be connectable and/or scalable to (the upper/inlet end of) the insert's inlet passage, e.g. to prevent leaks and/or air from entering the inlet passage. The outlet end of the cover/lid's or flow chamber's inlet passage may be configured to seal to the inlet passage of the insert, or vice versa. For example, the outlet end of the cover/lid's or flow chamber's inlet passage may be configured to provide an interference fit with, around or within the inlet end of the insert's inlet passage, or vice versa. Alternatively, the outlet end of the inlet passage of the cover/lid or flow chamber may be connectable to the inlet passage of the insert by a sealing element. The device may comprise a sealing element to seal the outlet end of the inlet passage of the cover/lid or flow chamber to the inlet passage of the insert when the cover/lid is connected to the drip chamber or when the insert is inserted into the flow chamber. The sealing element may be or comprise a sealing ring that can fit between the insert and the cover/lid or flow chamber. The cover/lid of the flow chamber may comprise the sealing element. For IV administrations, the cover/lid may be or comprise a standard vented or non-vented spike/piercing device for inserting into or piercing a liquid container, as is known in the art. The inlet passage of the cover/lid may extend through the spike/piercing device. Alternatively, where the drip chamber does not comprise a cover/lid, the drip chamber may comprise the spike or piercing device.

The cover or lid may be configured to close and seal the opening of the flow chamber by an interference fit. Alternatively or additionally, a sealing element that can fit between the drip chamber and the cover/lid, such as a sealing ring, may be used. The sealing element used for sealing the inlet passage of the cover/lid to the inlet passage of the insert and the sealing element used to seal the cover/lid to the drip chamber may be an integral sealing element, or separate sealing elements.

The device may further comprise one or more filter elements for filtering liquid upstream of the insert. The filter element(s) may be configured to fit between the insert and the cover/lid, and to cover at least the inlet end of the inlet passage of the insert. The filter element(s) may further be configured to provide a seal between the inlet passage of the insert and the inlet passage of the cover/lid. The sealing element may comprise the filter element(s), or vice versa. Where the insert comprises a filter element, a separate filter element may not be required. The cover/lid may be separate to the insert. Alternatively, the insert may comprise the cover/lid.

According to a third aspect of the invention, there is provided an IV administration set comprising one or more inserts according to the first aspect. The set may comprise one or more flow meter devices according to the second aspect. The set may further comprise one or more at least partially transparent drip chambers for receiving the insert. The drip chamber(s) may be standard drip chamber(s) for use in IV administration, as is known in the art. The drip chamber(s) may comprise an outlet for receiving a liquid flow from the outlet of the insert, e.g. located downstream of the outlet of the insert. The set may further comprise one or more covers or lids for the drip chamber(s). The cover(s)/lid(s) may comprise a means for connecting the inlet passage of the insert to a liquid source. The cover(s)/lid(s) may comprise an inlet passage with an outlet end for connecting to the inlet passage of the insert and an inlet end for connecting to a liquid source. The cover(s)/lid(s) may be or comprise a standard vented or non-vented spike for piercing a liquid source, such as an IV bag or rigid container, as is known in the art.

Alternatively, the drip chamber(s) may comprise a cover/lid. The drip chamber may comprise an inlet passage with an outlet end for connecting to the inlet passage of the insert and an inlet end for connecting to a liquid source. The drip chamber may further comprise a means for connecting the inlet passage of the insert to a liquid source, such as a spike or piercing device. The drip chamber may be a single piece drip chamber, or a multi-part drip chamber, e.g. comprising an upper and a lower portion that are connectable to each other.

The set may further comprise tubing for connecting the outlet of the drip chamber(s) to a point of administration. The set may further comprise one or more flow control devices. The flow control device(s) may be or comprise a clamp device for clamping the tubing, such as a roller clamp valve or pinch clamp valve as is known in the art. Alternatively, the flow control device(s) may be for connecting in line with the tubing. The IV administration set may be used with or comprise other standard accessories known in the art, including but not limited to, three-way stopcocks, injection ports, cannulae, luer locks and/or shut-off clamps.

The outlet end of the inlet passage of the cover(s)/lid(s) may be connectable to the inlet passage of the insert by an interference fit. Alternatively, the outlet end of the inlet passage of the cover(s)/lid(s) may be connectable to the inlet passage of the insert by a sealing element.

The set may further comprise one or more filter elements for filtering a liquid flow upstream of the insert. The filter element(s) may be configured to fit between the insert and the cover(s)/lid(s) and cover at least the inlet end of the inlet passage of the insert. Optionally or preferably, the sealing element may comprise the filter element.

According to a fourth aspect of the invention, there is provided a method of using an insert according to the first aspect, a method of using a flow meter device according to the second aspect, and/or a method of using the IV administration set according to the third aspect.

The method may comprise inserting an insert into an opening in a drip chamber or flow chamber. The method may further comprise attaching a cover or lid to the opening of the drip chamber or flow chamber to close and/or seal the drip/flow chamber. Attaching the cover/lid may further comprise positioning a filter element between the inlet end of the insert's inlet passage and the outlet end of the cover/lid's inlet passage. Attaching the cover/lid may further comprise connecting and/or sealing the inlet end of the insert's inlet passage to the outlet end of the cover/lid's inlet passage. The method may further comprise connecting the inlet end of the cover/lid's inlet passage to a liquid source. The step of connecting to a liquid source may comprise piercing a liquid container with a spike or piercing device of the cover/lid. The method may further comprise connecting tubing to the outlet of the drip/flow chamber to direct liquid flow to a point of use/administration. The method may further comprise flowing a liquid through the flow meter device. The method may further comprise reading a flow rate from the flow indicating channel.

The step of inserting the insert into the drip chamber or flow chamber may comprise inserting the insert to form the flow-resistant passage and/or the flow indicating channel between the insert and a wall of the drip chamber or flow chamber. The step of inserting may comprise inserting the insert to close and/or seal the one or more recesses or open channels in the mating surface of the insert against a wall of the drip chamber or flow chamber.

Features which are described in the context of separate aspects and/or embodiments of the invention may be used together and/or be interchangeable. Similarly, where features are, for brevity, described in the context of a single embodiment, these may also be provided separately or in any suitable sub-combination. Features described in connection with the device may have corresponding features definable with respect to a method, and these embodiments are specifically envisaged.

BRIEF DESCRIPTION OF DRAWINGS

In order that the invention can be well understood, embodiments will now be discussed by way of example only with reference to the accompanying drawings, in which:

FIG. 4b shows the outline of the one or more recess or open channels in the insert of FIG. 4a;

FIGS. 4c and 4d show, respectively, schematic horizontal and vertical cross-sections of the orifice of the flow-resistant passage of FIG. 4a;

FIGS. 4e and 4f show schematic vertical cross-sections of alternative orifice geometries;

Figures 1A, 1B:
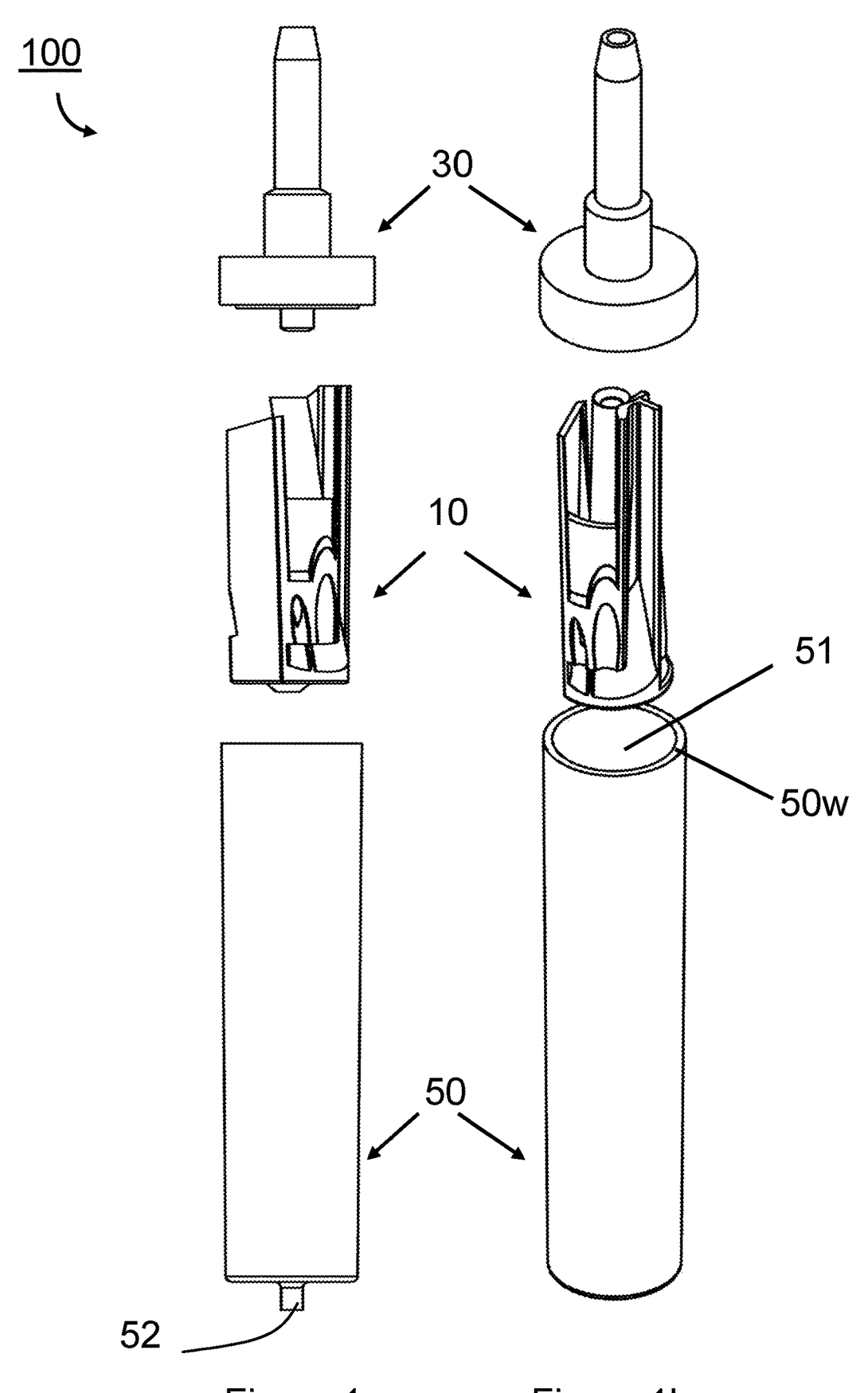
FIGS. 1a and 1b show, respectively, an exploded side and perspective view of a flow meter device according to the present invention.
Figure 2:
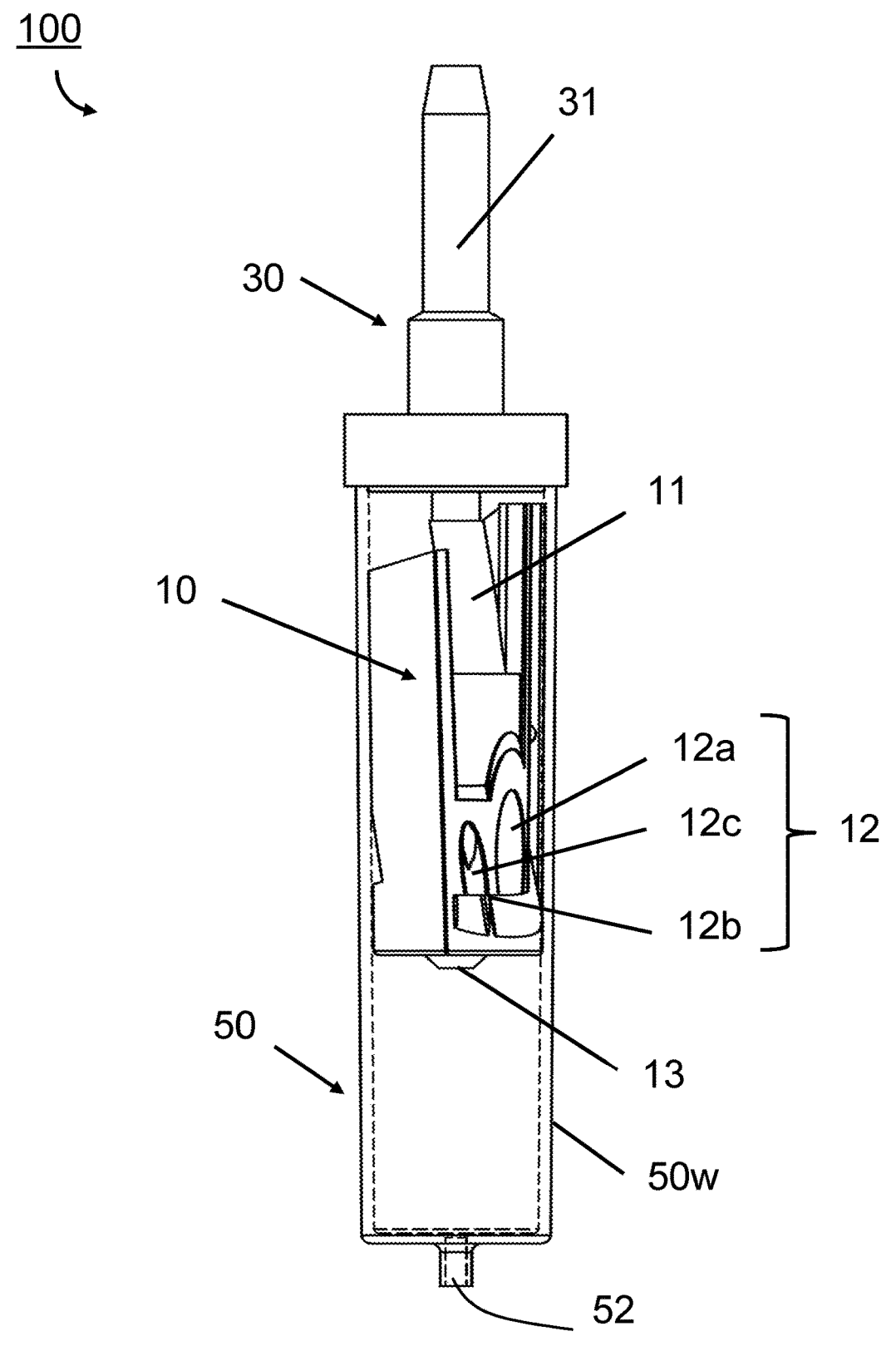
FIG. 2 shows a side view of the assembled flow meter device of FIG. 1 with the insert visible.

It should be noted that the figures are diagrammatic and may not be drawn to scale. Relative dimensions and proportions of parts of these figures may have been shown exaggerated or reduced in size, for the sake of clarity and convenience in the drawings. The same reference signs are generally used to refer to corresponding or similar features in modified and/or different embodiments.

DETAILED DESCRIPTION

FIGS. 1a-3b show a flow meter device 100 according to an aspect and/or embodiment of the invention. The device 100 comprises a flow metering insert 10, a flow chamber or housing 50 for receiving the insert 10 and a cover or lid 30 for closing/scaling the flow chamber 50 and connecting the device 100 to a liquid source (not shown). The device 100 is assembled by inserting the insert 10 into the flow chamber 50 and attaching the cover or lid 30 to the flow chamber 50 to close and/or seal the flow chamber 50. The device 100 is configured to be arranged substantially vertically in use, such that liquid can flow downwards through the device 100 under gravity. References to "upper" and "lower" below refer to this orientation, but it will be appreciated that aspects and embodiments of the invention are not limited to a particular orientation.

In the embodiment shown, the flow chamber 50 is a generally tubular member, comprising an opening, recess or bore 51 at an upper end to accommodate the insert 10 and an outlet 52 at a lower end for connecting to further components downstream of the device 100, such as tubing and/or a flow control device (not shown). The opening, recess or bore 51 defines an interior volume or space of the chamber bounded by a sidewall 50w. It will be appreciated that the flow chamber 50 is not limited to the geometry shown, e.g. exterior of the wall 50w may have a regular or irregular shape, and the interior volume of the drip chamber 50 may be substantially cylindrical as shown or non-cylindrical, provided there is at least a portion that can accommodate and cooperate with the insert 10, as described below. The cover or lid 30 comprises an inlet passage 32 for receiving a liquid flow from a liquid source. In the example shown, the inlet passage 32 is formed in a projection or spike 31 for connecting the device 100 to a liquid source, e.g. by inserting the spike 31 into an outlet of the liquid source, or piercing the liquid source. However, it will be appreciated that other means for fluidly connecting the device 100 to a liquid source can be used, such as push-fit, screw-fit or luer lock fittings known in the art. When connected to a liquid source, liquid enters the device 100 through the inlet passage 32 of the cover/lid 30, flows through the insert 10, into the flow chamber 50 and exits the device 100 through the outlet 52. The insert 10 provides a direct visual indication of the liquid flow rate through the device 100, as explained further below. As such, at least a portion of the flow chamber 50 must be formed or comprise a substantially or at least partially transparent material to enable at least a portion of the insert 10 to be visible through the sidewall 50w of the flow chamber 50.

In the embodiment shown, the flow chamber 50 is a standard drip chamber and the cover/lid 30 is a standard vented or non-vented spike/piercing device used in intravenous (IV) administration sets, as is known in the art.

The drip chamber 50 is constructed from a substantially transparent plastic material where at least a portion of the sidewall 50w (i.e. the lower portion below the insert) is substantially flexible/deformable such that liquid flow in the drip chamber 50 can be observed and the IV set can be primed in the usual way by squeezing and releasing the flexible/deformable portion of the drip chamber to draw liquid down from the liquid source and expel air upwards into the liquid source (e.g. an IV bag or container). The outlet end 32b of the cover/lid's inlet passage 32 is configured to be ISO8536-4 compliant (i.e. positioned 5 mm from interior surface of the sidewall 50w), and typically comprises a drip-forming orifice as traditionally it is used to form drops to indicate flow rate as viewed in the drip chamber 50. For example, the drip-forming orifice may be approximately 3 mm wide, or narrower or wider, depending on the required drop size/volume. However, it will be appreciated that the present invention is not limited to IV administration and, as such, generally any suitable flow chamber 50 sized to accommodate the insert 10 (with a substantially transparent sidewall 50w), and any suitable cover/lid 30 with a means to connect the device 100 to a liquid source may be used, particularly in non-IV applications.

Figures 3A, 3B:
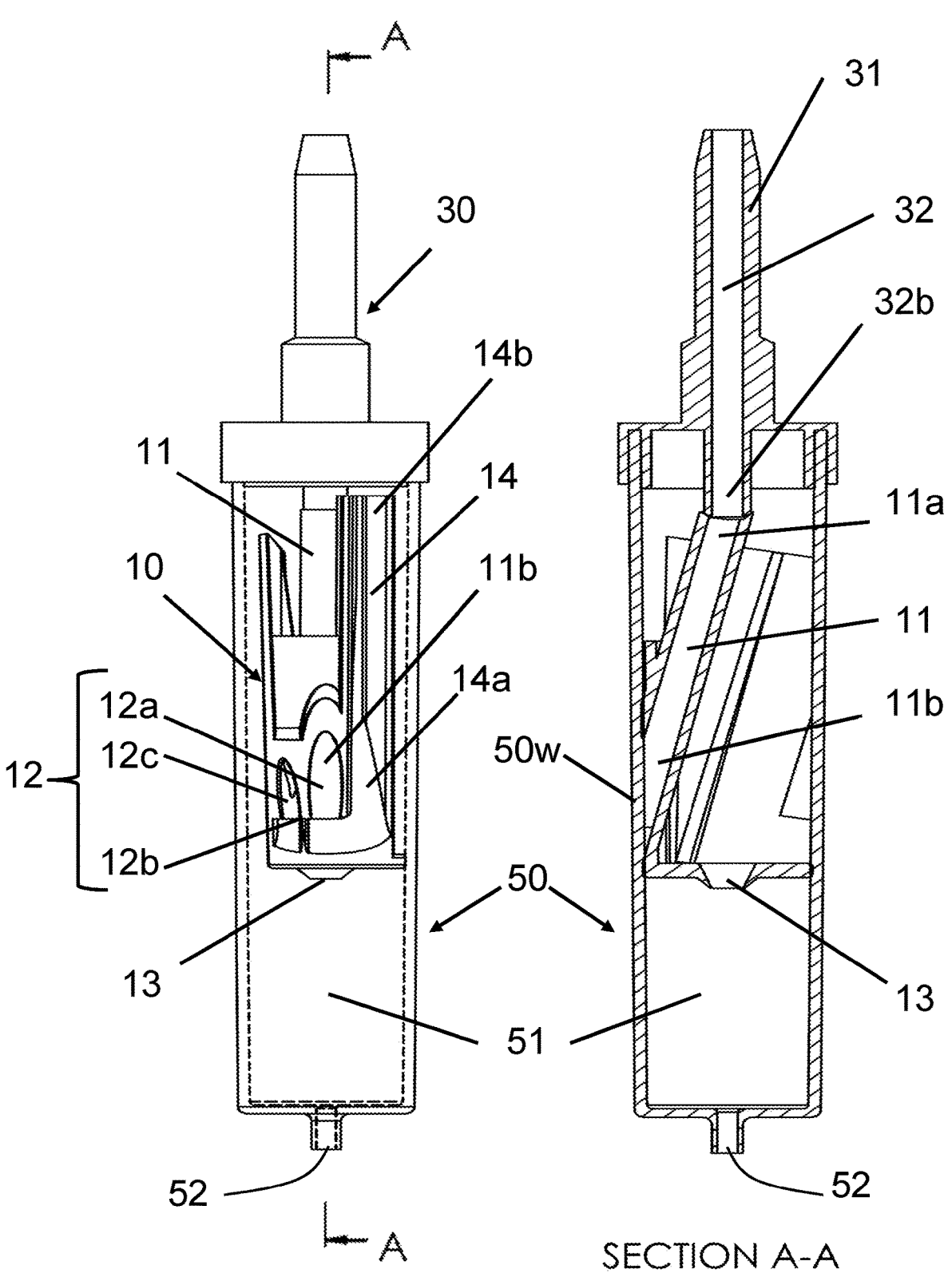
FIGS. 3a and 3b show, respectively, a further side view of the assembled flow meter device of FIG. 1 with the insert visible and a cross-sectional view.
Figure 4A:
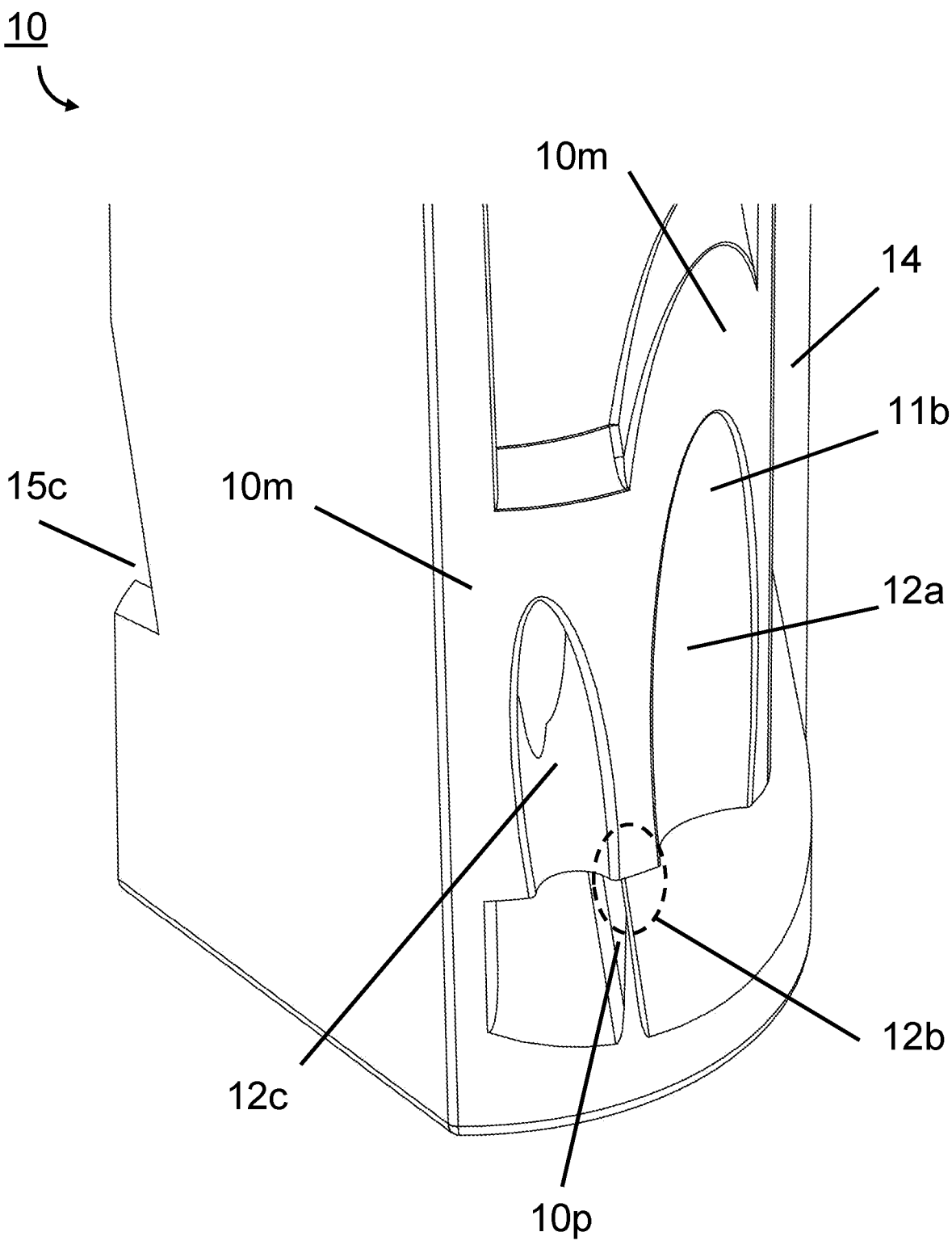
FIG. 4a shows a perspective view of detail of the insert of FIGS. 1-3.
Figures 5A, 5B:
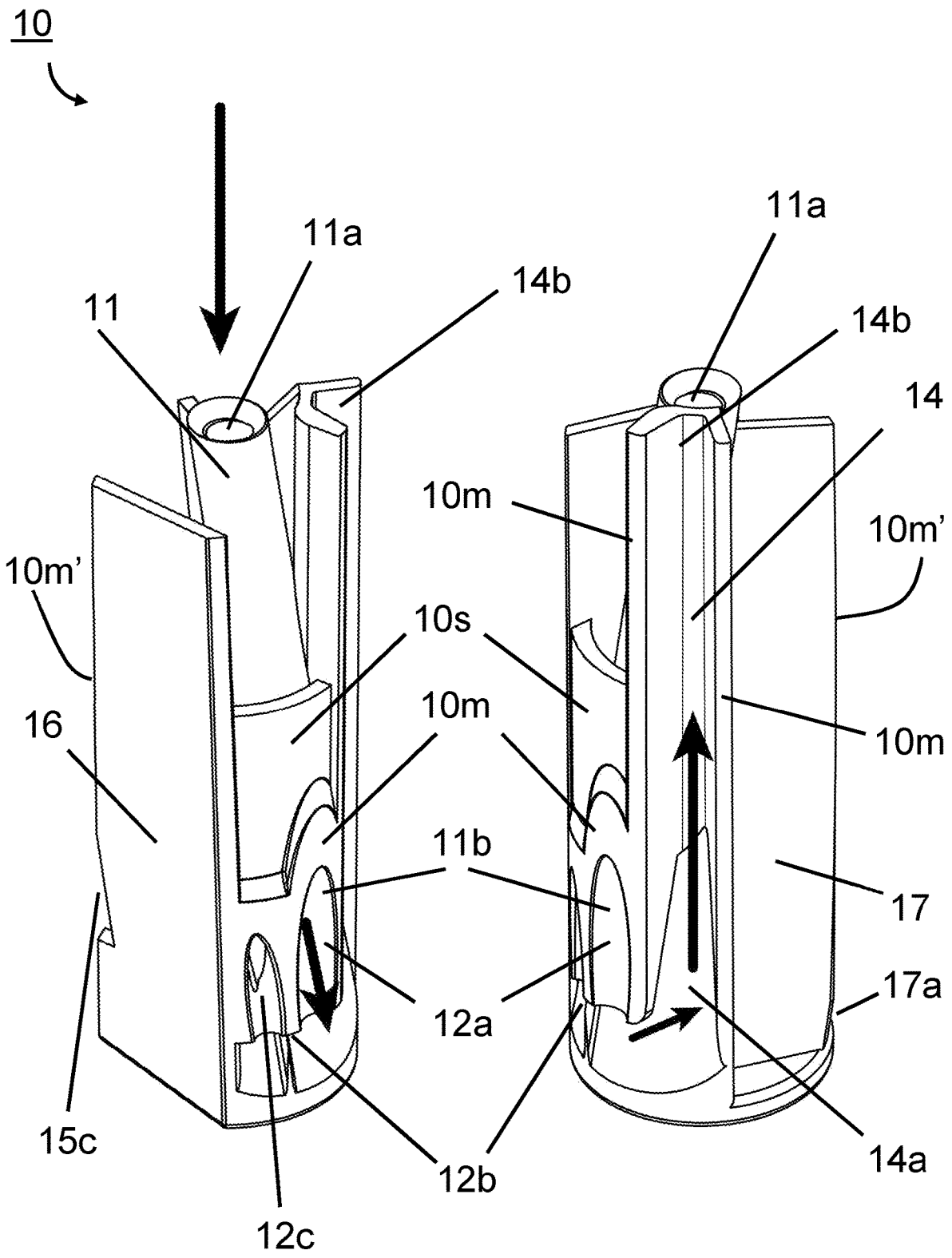
FIGS. 5a and 5b show, respectively, further perspective views of the insert of FIGS. 1-4 from different angles indicating the liquid flow paths.

FIGS. 4a, 5a and 5b show the insert 10 in more detail. The insert 10 comprises an inlet passage 11, an outlet 13 and a flow-resistant passage 12 between the inlet passage and the outlet 13. This defines a primary liquid flow channel through the insert 10. The insert 10 also comprises a flow indicating channel 14, the lower end/inlet 14a to which is connected between the inlet passage 11 and the flow-resistant passage 12. Attaching the cover/lid 30 to the drip chamber 50 connects the inlet passage 32 to an inlet end 11a (upper end) of the inlet passage 11 as shown in FIG. 3b, thus providing a passage for liquid flow from a liquid source to the inlet passage 11 of the insert 10. An interference fit or separate sealing element can be used to provide a liquid-tight seal between the inlet passage 32 of the cover/lid 30 and the inlet passage 11 of the insert 10, as is discussed further below.

The insert 10 has a length along a longitudinal axis that is less than the length of the drip chamber 50. For IV administration, the drip chamber 50 may have a length at least 40 mm greater than the length of the insert 10 and the outlet 13 of the insert 10 may be positioned at least 5 mm from (interior surface of) the sidewall 50w of the drip chamber 50, to comply with ISO-8536-4. However, it will be appreciated that for non-IV applications where compliance with ISO-8536-4 is not necessary, the insert 10 need only be equal to or shorter than the length of the drip chamber 50 to fit in it. In one example, the drip chamber 50 may be approximately 100 mm in length, and the insert 10 may be approximately 60 mm in length to be ISO-8536-4 compliant. In addition, the outlet 13 of the insert 10 may be or comprise a drip forming orifice (e.g. with an aperture approximately 3 mm wide), such that a flow of drops may still be visible in the drip chamber 50 as liquid exits the insert 10, in accordance with ISO-8536-4 (that requires drops to be continuously visible in gravity-fed infusion equipment for medical use). In an insert approximately 60 mm long, the inlet passage 11 may be approximately 40 mm in length, which may encourage laminar flow.

In a standard spike 30 used in IV administration, the outlet end 32b is typically chamfered. The inlet end 11a of the inlet passage 11 can be shaped to accommodate this and provide an interference fit with the outlet end 32, to connect and seal the inlet passage 11 of the insert to the inlet passage 32 of the cover/lid 30. Alternatively, a separate sealing ring may be provided to seal the interface between the inlet passage 11 of the insert and the inlet passage 32 of the cover/lid 30 when the cover/lid 30 is attached (not shown).

The flow-resistant passage 12 comprises an inlet end 12a, an outlet end 12c, and a flow-restricting orifice 12b between the inlet end 12a and the outlet end 12c. An outlet end 11b (lower end) of the inlet passage 11 is in communication with the inlet end 12a of the flow resistant passage 12. The lower end 11b of the inlet passage 11 is also in communication with the flow indicating channel 14. In particular, the flow indicating channel 14 comprises an inlet end (lower end) 14a in communication with the lower end 11b of the inlet passage 11 and the inlet end 12a of the flow-resistant passage 12, and extends generally upwardly from its lower end 14a to an open outlet end 14b (upper end), as shown in FIG. 3a. The open upper end 14b of the flow resistant channel 14 is in communication with the interior volume 51 of the drip chamber 50 (as well as the portion of the drip chamber 50 below the insert 10).

The flow-resistant passage 12 and the flow indicating channel 14 are partially defined by one or more recesses or open channels 10r in a surface 10m, as can be seen in FIGS. 4a, 5a and 5b. The outline of the one or more recesses or open channels 10r is shown by the bold line in FIG. 4b for greater clarity. The insert 10 is shaped and configured to have an interference fit within the drip chamber 50, such that the one or more recesses or open channels 10r are closed and sealed against the sidewall 50w of the drip chamber 50 when the insert 10 is inserted into the drip chamber 50. The interference fit is provided by one or more mating surfaces 10m, 10m' that are configured to contact the interior surface of the sidewall 50w when the insert 10 is inserted into the drip chamber 50. The one or more recesses or open channels 10r are formed in a mating surface 10m configured to contain, conform to and seal against the interior surface of the sidewall 50w when the insert 10 is inserted into the drip chamber 50. In this way, when the insert 10 is inserted into the drip chamber 50, the flow-resistant passage 12 and the flow indicating channel 14 are formed between the insert 10 and an interior surface of the sidewall 50w. The mating surface 10m may be configured to at least partially deform the interior surface of the sidewall 50w, and/or be at least partially deformed by the interior surface of the sidewall 50w, to conform and make a liquid-tight seal therebetween. For example, where the insert 10 is formed of or comprises a substantially rigid material, the sidewall 50w of the drip chamber 50 may be substantially flexible or less rigid than the insert, such that the interior surface of the sidewall 50w at least partially flexes or deforms to conform to the mating surface 10m of the insert 10 when the insert 10 is inserted into the drip chamber 50. Alternatively, where the insert 10 is formed of or comprises a substantially deformable material, the sidewall 50w of the drip chamber 50 may be substantially rigid, such that the mating surface 10m at least partially deforms to conform to the interior surface of the sidewall 50w. In either case, the mating surface 10m is configured such that it can conform (after deforming or not deforming) to the final interior surface of the sidewall 50w when the insert 10 is inserted into the drip chamber 50.

Figure 7:
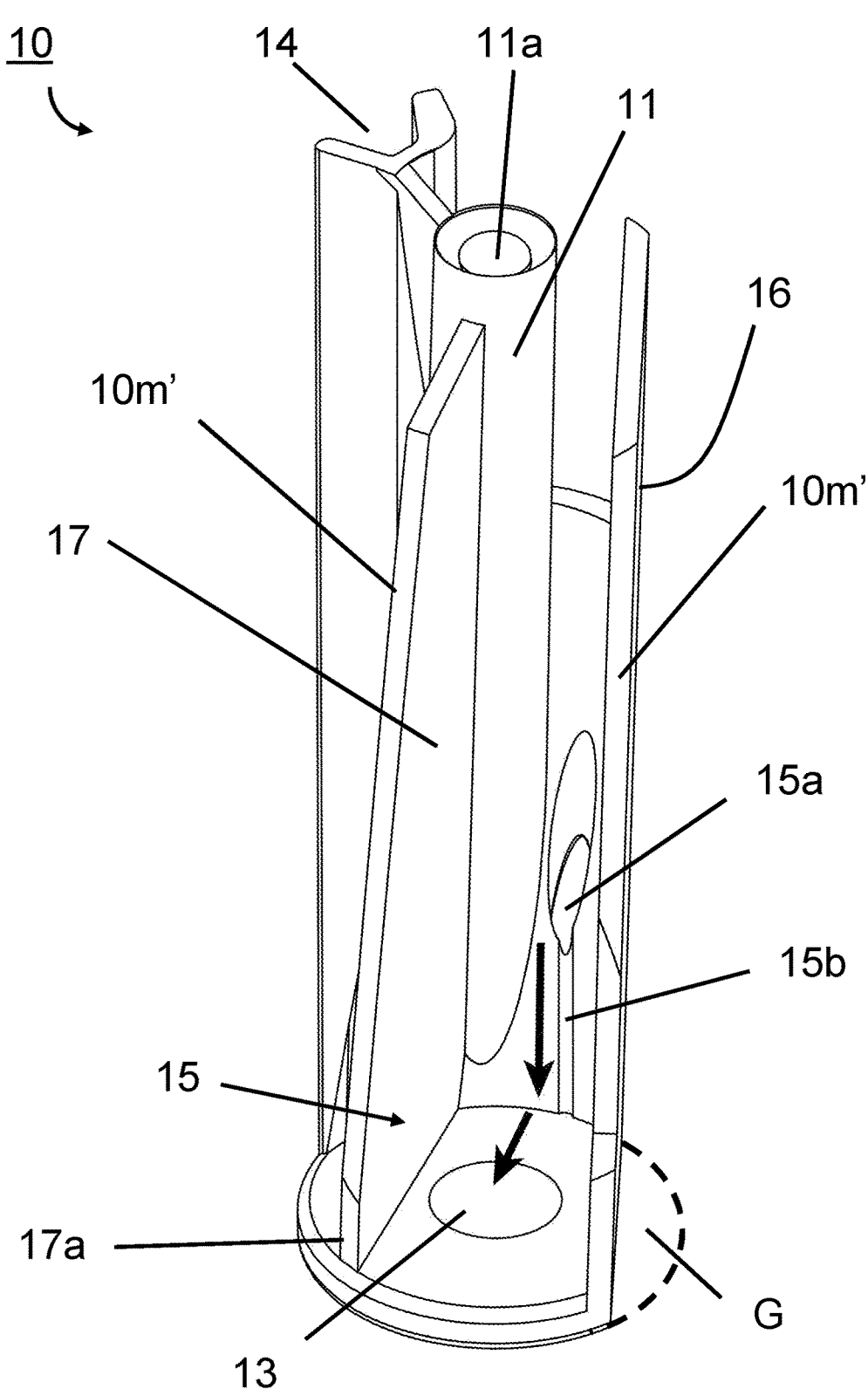
FIG. 7 shows further perspective views of the insert of FIGS. 1 to 6 from a different angle showing an exit chamber.

The mating surface 10m may extend at least partially around the side(s) of the insert 10, and/or further mating surfaces 10m' can be provided at different locations around the side(s) of the insert 10 to encourage a tight interference fit within the drip chamber 50. In the embodiment shown, further mating surfaces 10m' are provided on ribs or panels 16, 17 that extend towards and/or between the sidewall 50w, as seen in FIGS. 5a, 5b and 7. The mating surface 10m in which the flow-resistant passage 12 and the flow indication channel 14 are partially defined is a continuous and substantially smooth surface to provide a uniform sealing contact with the sidewall 50w and avoid leaks. Alternatively or additionally, the mating surfaces 10m, 10m' can be or comprise one or more sealing ribs that reduce the contact area and encourage a liquid-tight seal against the interior surface of the sidewall 50w of the drip chamber 50 (not shown). For example, the mating surface 10m may comprise one or more sealing ribs that extend around the (perimeter of the) one or more recesses or open channels (not shown). Scaling ribs may have a substantially rounded or triangular profile and may be configured to deform the interior surface of the sidewall 50w, or be deformed by the interior surface of the sidewall 50w, to make a liquid-tight seal therebetween.

The insert 10 may be formed of or comprise a substantially rigid material, such as acrylonitrile butadiene styrene (ABS) or any other substantially rigid plastic permitted for use in IV applications. In this case, the insert 10 may provide an interference fit within a substantially flexible/deformable portion of the drip chamber 50 to provide a liquid-tight seal therebetween. Alternatively, the insert 10 may be formed of or comprise a substantially flexible, deformable and/or compressible material, such as polyvinyl chloride (PVC) or any PVC-free equivalent plastic permitted for use in IV applications. In this case, the insert 10 may provide an interference fit within a substantially rigid portion of the drip chamber 50 to provide a liquid-tight seal therebetween.

Figure 6:
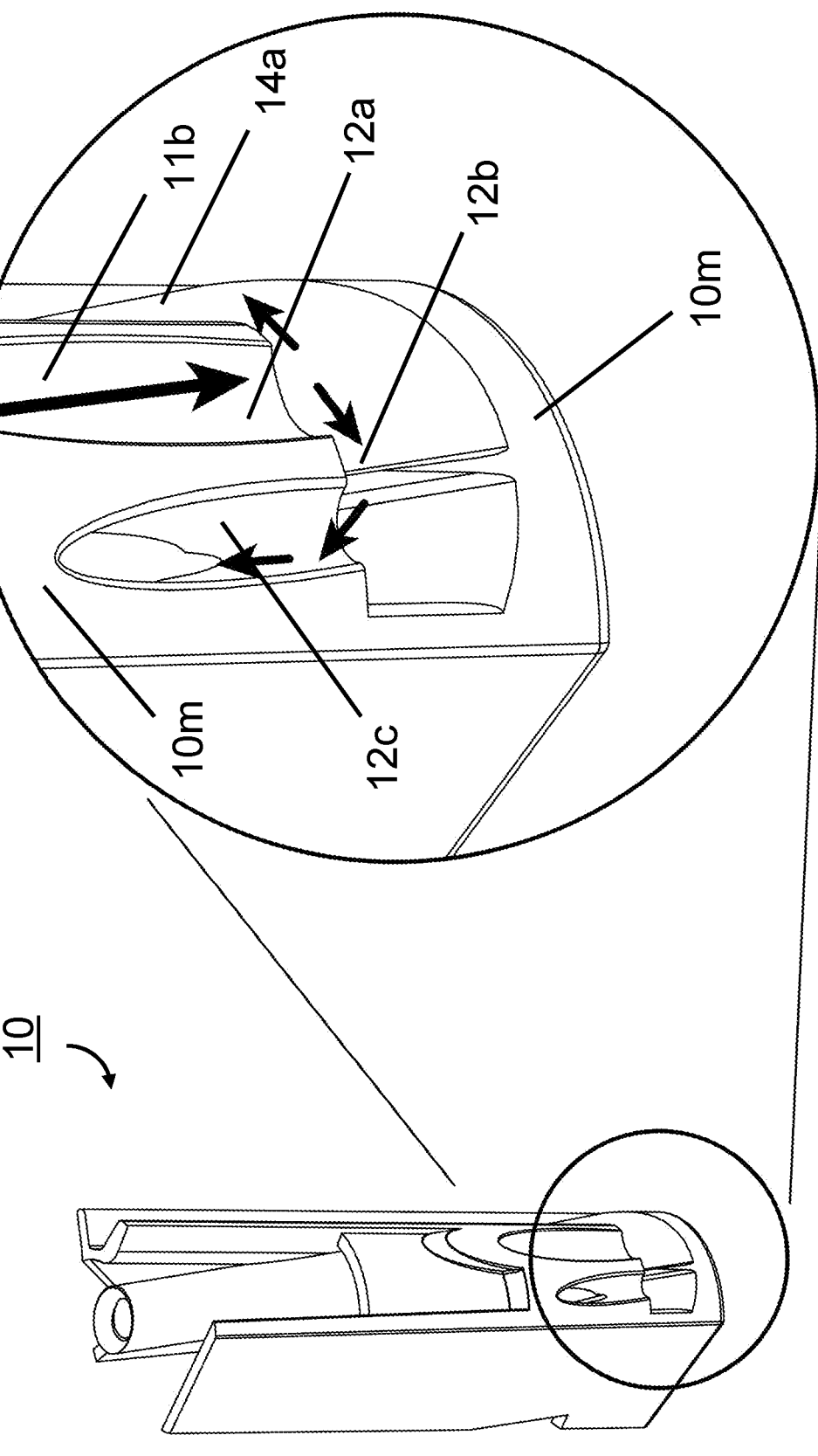
FIG. 6 shows an enlarged view of the insert of FIGS. 1-5 indicating the liquid flow paths.
Figure 8A:
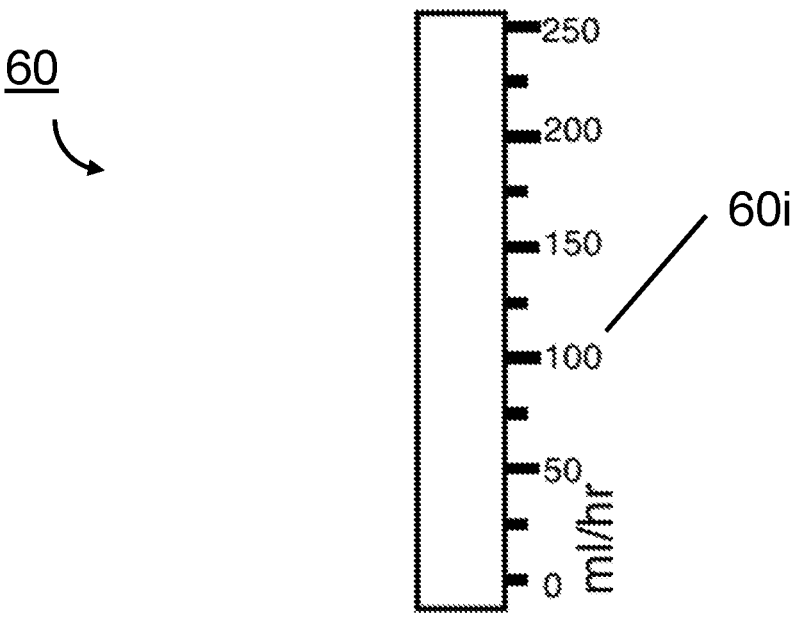
FIGS. 8a and 8b show graduated scales for measuring a flow rate.

In use, liquid flowing through the inlet passage 11 encounters the sidewall 50w of the drip chamber 50 and is forced towards the flow-resistant passage 12. The resistance to flow provided by the orifice 12b causes liquid to enter the adjoining flow indicating channel 14, as indicated by the arrows in FIGS. 5a and 5b. This liquid flow through the insert 10 is further illustrated by the arrows in FIG. 6. The liquid level or height in the flow indicating channel 14 will rise to a height proportional to the liquid flow rate through the flow-resistant passage 12 (explained further below), which may be regulated by an external flow control device (not shown). A scale 60 with calibrated indices 60i may be placed on, alongside or next to the flow indicating channel 14 to provide a clear reading of liquid flow rate, as shown in FIG. 8a. A visible float may also be provided in the flow indicating channel 14 to facilitate reading of the liquid level/scale 60. The insert 10 or the drip chamber 50 may comprise the scale 60, as required.

The operating principle of the device 100 is the following: The flow-resistant liquid passage 12 provides resistance to liquid flow and an associated pressure drop according to the width of the orifice 12b and the liquid flow rate. When liquid flows through the orifice 12b, its pressure builds up slightly upstream of the orifice 12b before dropping on the downstream side of the orifice 12b and eventually rising again further downstream as the flow expands. The pressure P at the bottom of the column of liquid in the flow indicating channel 14 is given by $P=\rho gh$, where $\rho$ is the liquid density, g is the gravitational constant, and h is the liquid height. Thus, the resistance to flow caused by the orifice 12b causes the liquid upstream to back up, enter the flow indicating channel 14 and reach a height h according to the pressure drop. The flow rate through the orifice 12b is substantially the same as the flow rate in the rest of the primary liquid flow channel 12. The rate of liquid flow through the device 100 can therefore be read directly from the level/height of liquid in the flow indicating channel 14 via the scale 60 (unless the flow rate is high enough to overflow the indicating channel 14, as discussed below).

In an embodiment, the orifice 12b has a width of between substantially 0.1 mm-0.2 mm. This may provide a suitable resistance to flow to provide a discernible change in liquid level/height in the flow indicating channel 14 for flow rates in the range of approximately 0-250 ml/hour, covering a scale 60 of approximately 40 mm. However, it will appreciated that other orifice widths can be used, dependent on the application of the device 100 (e.g. the scale size required and/or the flow rates to be measured). The use of an orifice restriction (rather than an elongate restriction, such as a narrow pipe/tube section) may make the flow meter device 100 less susceptible to changes in viscosity of the liquid. As such, preferably the orifice 12b is as close to having no length (in the direction of flow) as possible (within the constraints of the manufacturing process). As seen in FIGS.

Figures 4B, 4C, 4D, 4E, 4F:
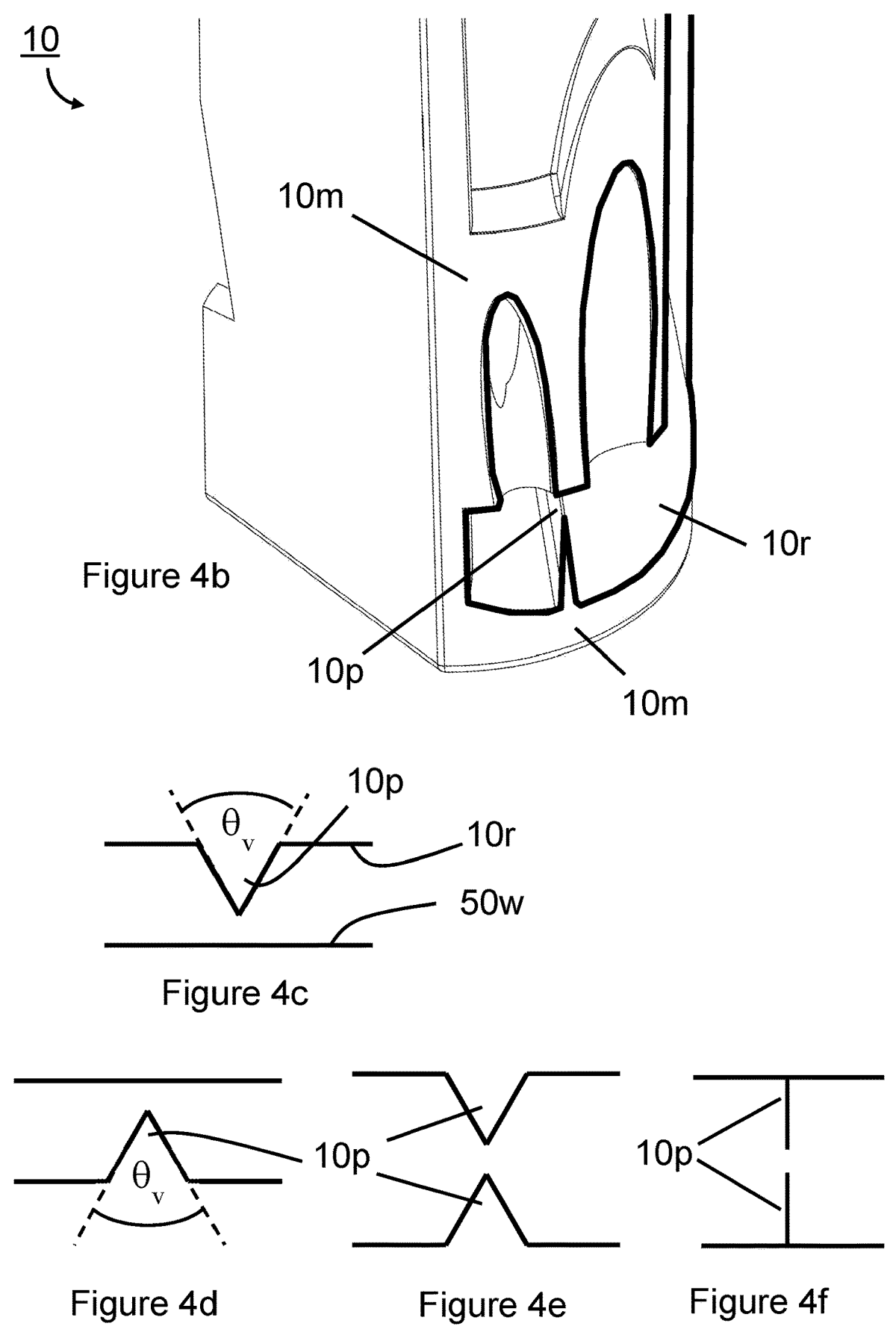

4a and 4b, the orifice 12b is formed by a substantially V-shaped projection 10p extending from a wall of the recess 10r or flow-resistant passage 12 that narrows the width of the passage. In horizontal cross-section, the projection 10p extends from a floor of the recess 10r and opposes the wall 50w of the drip chamber 50, as shown in FIG. 4c. Additionally, the projection 10p can extend, in vertical cross-section, from a sidewall of the recess 10r or flow-resistant passage 12 towards a substantially straight portion of an opposing recess sidewall, as shown in FIG. 4d. Alternatively, the orifice constriction 12b may be formed by two opposing projections 10p in vertical cross-section, as shown in FIG. 4e. Ideally, the orifice 12b would be formed by one or more thin-wall projections 10p extending at least partially across the flow-resistant passage 12, as shown in FIG. 4f. However, V-shaped projections 10p are a compromise between performance and manufacturability. The more acute the angle $\theta_v$ of the sidewalls forming the projection(s) 10p the more ideal the orifice 12b becomes and the less susceptible the flow meter device 100 is to changes in viscosity of the liquid (see FIGS. 4c and 4d).

The flow-resistant liquid passage 12 is substantially U-shaped (when the insert 10 and device 100 are arranged substantially vertically), such that the direction of liquid flow is substantially reversed on its passage through the flow-resistant liquid passage 12. The orifice 12b is located towards the bottom of the U-shaped flow-resistant liquid passage 12. The U-shaped flow-resistant liquid passage 12 provides that, when liquid flow is stopped by an operator, liquid remains in the flow-resistant liquid passage 12. This prevents the orifice 12 from drying out, which may lead to a build-up of solid deposits or crystals that may alter the size of the orifice 12b and adversely affect its function. For example, a reduction in the orifice 12b width would introduce error in the reading of liquid flow in the flow indicating channel 14, and eventual blocking of the orifice 12b would prevent liquid flow in the insert 10 altogether.

After passing the orifice 12b, liquid flows substantially upwards to the outlet end 12c of the flow-resistant passage 12 and through an opening 15a into an exit chamber 15, as shown in FIG. 7. This flow through a submerged orifice 12b prevents drops forming during the restricted part of the flow. The purpose of the exit chamber 15 is to direct liquid flow to the outlet 13, which is formed in the floor of the exit chamber 15. The opening 15a is positioned above the level/height of the outlet 13 when the insert 10 is arranged substantially vertically such that liquid drains downward to the outlet 13. The exit chamber 15 comprises a narrow channel 15b extending from the opening 15a to the floor of the exit chamber 15. The narrow channel 15a draws liquid downwards into the exit chamber by capillary action. As such, as the liquid flows from the opening 15a to the outlet 13, it is prevented from forming irregular drops that may make the flow rate measurement unreliable. The narrow channel 15b may be a closed channel or an open channel. In the embodiment shown, the narrow channel 15b is an open channel. The narrow open channel 15b may be formed by a recess in a sidewall of the exit chamber 15 and thus can easily be formed by regular moulding processes. The narrow open channel 15b is ideally semi-circular in cross section, with a width of less than 1 mm (approximately 0.5 mm).

The exit chamber 15 comprises an overflow opening 15c in communication with the interior volume 51 of the drip chamber 50 (in particular, the portion of the drip chamber 50 below the insert 10). The overflow outlet 15c is positioned between the levels/heights of the outlet 13 and the opening 15a to prevent liquid filling up in the exit chamber 15 which would otherwise introduce error to the measurement of flow rate, particularly the "zero line", from the flow indicating channel 14. In the embodiment shown, the overflow opening 15$c$ is formed by a notch in the panel 16 and the exit chamber 15 open to the interior volume 51 of the drip chamber 50, such that it does not enclose a space. The open exit chamber 15 and/or the overflow opening 15$c$ permits air flow between the exit chamber 15 and the low portion of the drip chamber 50. This prevents air locks and allows the device 100 to be "primed" in the same manner as existing drip sets, which involves squeezing and releasing the lower portion of the drip chamber 50 to draw liquid down through the primary liquid passage from the liquid source and expel air upwards into the liquid source.

The insert 10 may further be shaped and configured to provide a gap G between insert 10 and the sidewall 50$w$ of the drip chamber 50 extending the length of the insert 10. The gap G may further aid air flow between the exit chamber 15 and the interior volume 51 of the drip chamber 50 (and thus 'priming', as discussed above). In the embodiment shown, the gap G is provided by the panel 16 which forms a chamfered side 16 of the insert 10, as seen in FIG. 7. The dashed line in FIG. 7 indicates the location of the sidewall 50$w$ when insert 10 is inserted into the drip chamber 50 and the resulting gap G formed between the sidewall 50$w$ and the panel 16.

The inlet passage 11 may include a filter element (not shown) to filter liquid before reaching the flow-resistant passage 12 and prevent any blockages by particulates contained in the liquid. The filter element may be provided at or near the upper end 11$a$ of the inlet passage 11. The filter element may be integral with the insert 10. Alternatively or additionally, the device 100 may comprise a separate filter element that can be fitted between the insert 10 and the cover/lid 30 and/or between the drip chamber 50 and the cover/lid 30. Such a filter element may be integrated with a sealing ring (where present) to seal the interface between the inlet passage 32 of the cover/lid 30 and the inlet passage 11 of the insert 10 and/or the interface between the cover/lid 30 and the upper end of the drip chamber 50. For example, the device 100 may comprise a flexible insert ring containing a filter element (not shown).

Figure 8B:
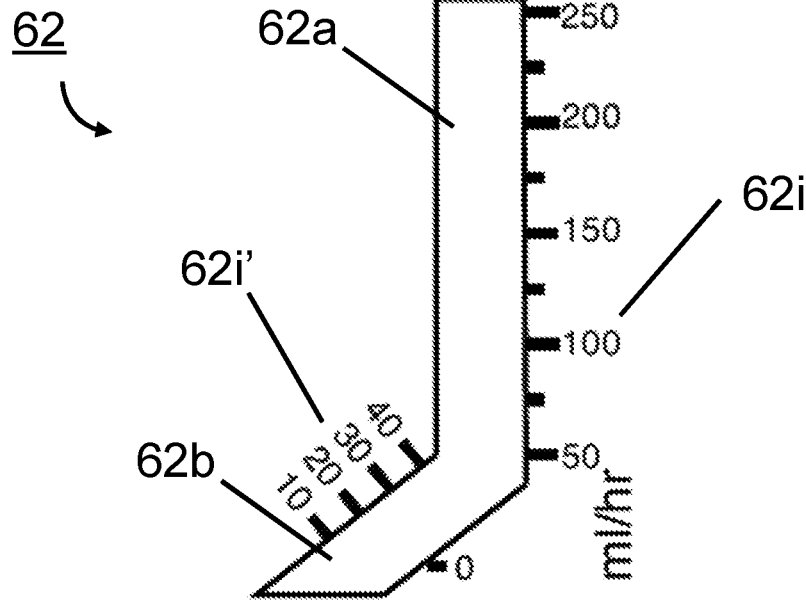

FIGS. 8$a$ and 8$b$ show example scales 60, 62 that can be used to indicate a flow rate from the liquid level/height in the flow indicating channel 14. A visible float (not shown) can be also provided in the flow indicating channel 14 to improve the legibility of the scale. In the embodiment shown in FIGS. 1-7, the flow indicating channel 14 has a substantially constant horizontal cross-section, is substantially straight, and extends substantially vertically from its lower end 14$a$, when the insert 10 is arranged substantially vertically. In this case, a linear scale 60 with regularly spaced indices 60$i$ can be used to indicate the flow rate from the liquid level/height, as shown in FIG. 8$a$. However, it will be appreciated it is not essential for the flow indicating channel 14 to be straight, vertical, and/or have a constant horizontal cross-section with liquid level/height.

In another embodiment (not shown) the flow indicating channel 14 can extend upwardly from its lower end 14$a$ at an angle θ to vertical (or the longitudinal axis of the insert 10), e.g. 0-45 degrees from vertical, and a similar scale 60 can still be used. In this case, the flow indicating channel 14 is also curved about the axis of the insert due, following the curvature of the sidewall 50$w$ of the drip chamber 50. Angling the flow indicating channel 14 stretches the scale by a factor 1/cos(θ), which can allow a more detailed scale to be used (i.e. with a greater number of indices 60$i$ and/or smaller flow rate increments), thereby reducing the relative error in the flow rate reading. More accurate flow rate measurements are typically required at low flow rates (e.g. less than 50 ml/hour) where the relative error increases (since the measured value decreases). Low flow rates correspond to low liquid levels/heights. As such, in another embodiment (not shown), to increase the measurement accuracy at low flow rates, the flow indicating channel 14 comprises a lower portion extending upwards from its lower end 14$a$ at an angle θ to vertical (e.g. 0-45 degrees) and an upper portion that extends substantially vertically from the lower portion. FIG. 8$b$ shows an example angled scale 62 that can be used with such a flow indicating channel 14. The scale 62 comprises an upper portion 62$a$ with a first set of indices 62$i$ and a lower portion 62$b$ with a second set of indices 62$i'$ that are different to the first set 62$i$.

In another embodiment (not shown), the flow indicating channel 14 can curve away from the longitudinal axis of the insert 10, e.g. when viewed from the side of the insert 10. Angling and/or curving the flow indicating channel 14 with respect to the longitudinal axis may allow the length of the insert to be reduced.

Figure 10:
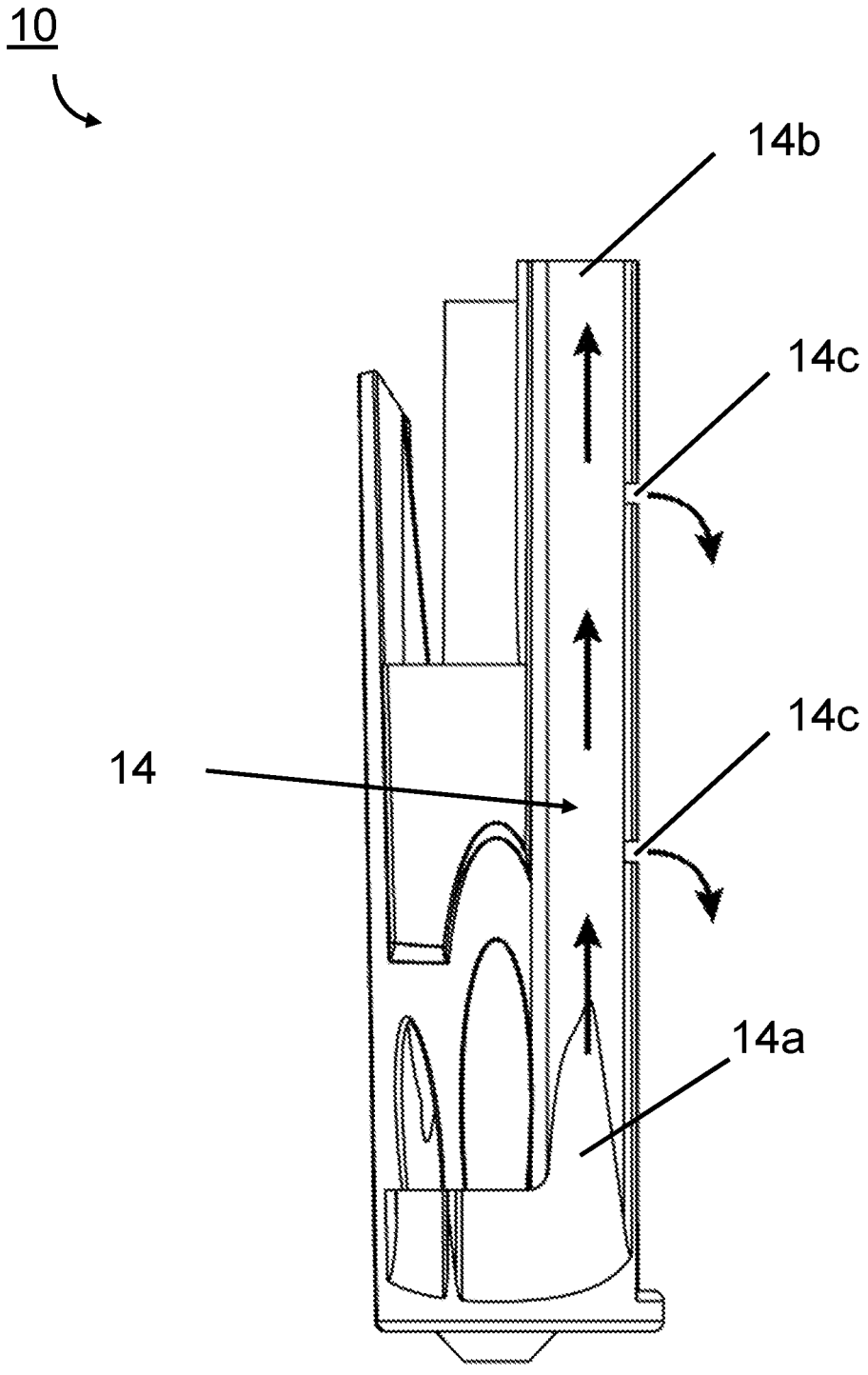
FIG. 10 shows another example insert for the device of FIG. 1.

Alternatively or additionally, one or more notches or openings 14$c$ may be formed in a wall of the flow indicating channel 14, such that as the liquid level rises above the notch 14$c$, some of the liquid escapes (into the drip chamber 50) via the notch 14$c$, as shown in FIG. 10 where the arrows indicate the liquid flow in the flow indicating channel 14. The presence of such a notch 14$c$ means that much higher flow rates are needed for the liquid level in the flow indicating channel 14 to continue to rise above the notch 14$c$. Above the notch 14$c$, the liquid level is dependent on the regular fluid mechanics due to flow resistance by the orifice 12$b$ and also the liquid loss from the flow indicating channel 14 via the notch 14$c$. This provides for a non-uniform or non-linear scale, with more flow sensitivity below the notch 14$c$, and less flow sensitivity above it. This notch 14$c$ feature may be repeated as desired along the flow indicating channel 14. A nonlinear scale may be desirable in instances where higher flow measurement accuracy is required at lower flow rates, but the same flow meter must also measure high flow rates. A linear scale in such instances may be impractically large.

At high flow rates (e.g. greater than 250 ml/hour), liquid may exceed the height of the flow indicating channel 14 and flow out of the open upper end 14$b$ into the drip chamber 50 where it may leave the device 100 through the outlet 52. As such, the open upper end 14$b$ also serves as an overflow to allow liquid to continue to flow freely through the device 100 under high flow conditions. For example, although a scale 60, 62 from 0-250 ml/hour may be provided for the flow indicating channel 14 (as shown in FIGS. 8$a$ and 8$b$), a much greater flow rate, e.g. 3000 ml/hour or more, may still be achieved by the device 100 (the scale being unnecessary at such high flow rates). If control of flow at rates greater than those measurable by the flow indicating channel 14 is required, drops exiting the drip forming orifice of the outlet 13 may be counted as per known drop counting methods of measuring flow rate in a drip chamber 50 (provided the flow rate is not so high that drops are no longer formed, see below). At very high flow rates (e.g. during resuscitations), the liquid flow exiting orifice 13 will form a steady stream rather than separated drops. This is consistent with regular IV drip sets (without the insert 10), where the operator would expect a stream of flow from the orifice 32$b$ of the spike 30 instead of drops to check that free flow is occurring.

Figure 11:
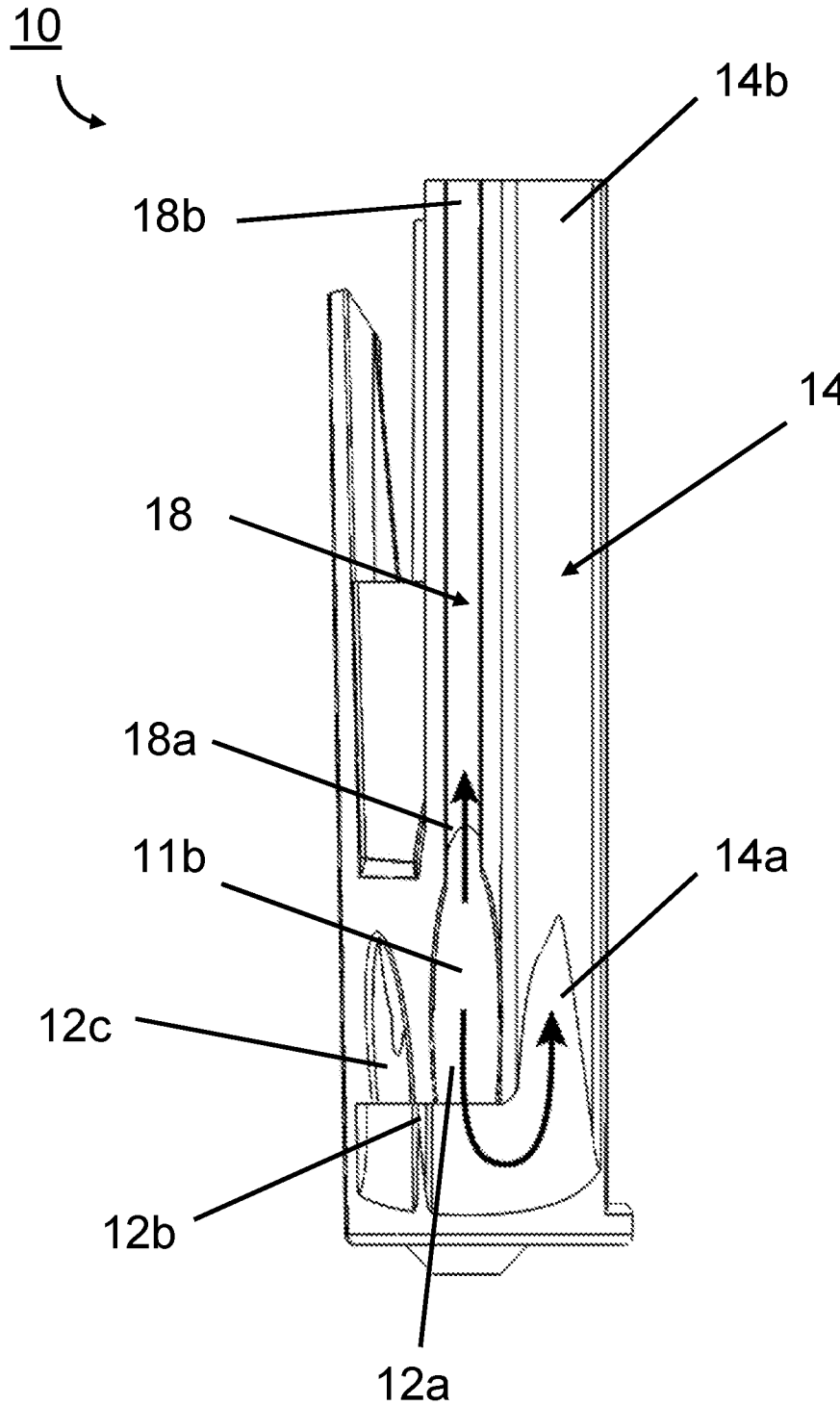
FIG. 11 shows another example insert for the device of FIG. 1.

FIG. 11 shows an embodiment of the insert 10 further comprising a vent channel 18. The vent channel 18 is a substantially vertical column running parallel to the flow indicating channel 14 with a lower end 18a in fluid communication with the lower/outlet end 11b of the inlet passage 11 and an open upper end 18b, as shown. The vent channel 18 is configured to allow any bubbles in the liquid flowing out of the inlet passage 11 to rise upwards in the vent channel 18, rather than entering the flow indicating channel 14 which would adversely affect the flow rate measurement/reading. It will be appreciated that liquid as well as any bubbles flows up the vent channel 18. If there were no bubbles in the liquid flow exiting the inlet passage 11, the liquid would rise and fall at the same level in both the flow indicating channel 14 and the vent channel 18. However, the vent channel 18 may also have bubbles in, and thus the liquid level in it should be ignored. Importantly, this means the liquid level in the flow indicating channel 14 is substantially bubble-free and provides an accurate flow rate reading. The upper end 18b of the vent channel 18 is at least the same height as the upper end 14b of the flow indicating channel 14 to prevent any overspill/overflow of fluid (liquid and gas/bubbles) from the vent channel 18 from affecting liquid levels higher than the upper end 18b of the vent channel 18 in the flow indicating channel 14. For example, if the upper end 18b of the vent channel 18 were below the upper end 14b of the flow indicating channel 14, this would effectively act like a notch 14c, as described above, such that any liquid height in the flow indicating channel 14 above the upper end 18b in this instance would reflect the resistance to flow by the orifice 12b (standard indication mechanism) and the fluid losses out of the end 18b, much like the notch 14c described above.

Figure 9:
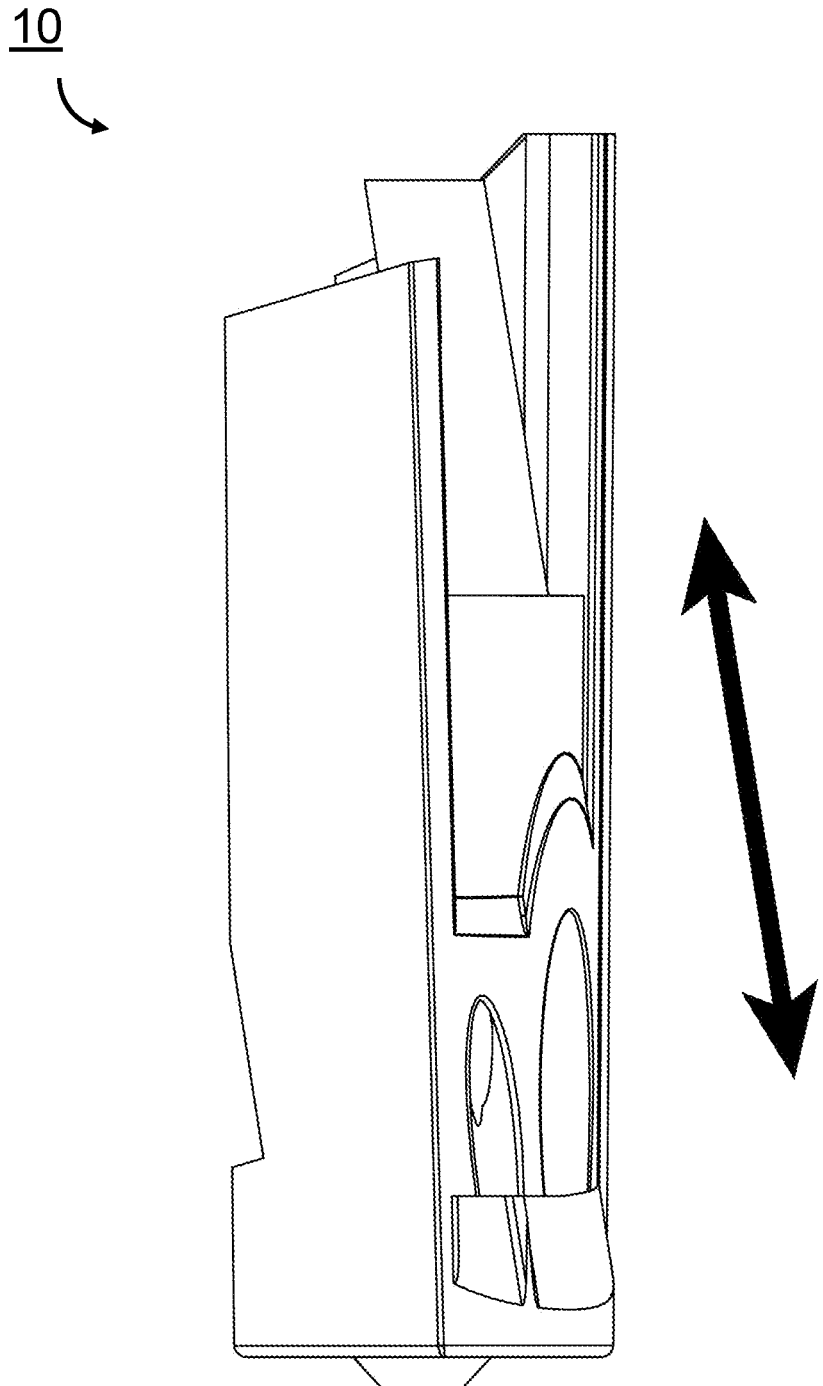
FIG. 9 shows a further perspective view of the insert of FIGS. 1 to 7 indicating the moulding direction.

The insert 10 can be formed by an injection moulding process. In the embodiment shown, it is shaped such that it can be moulded using a single direction moulding process, as indicated by the arrow in FIG. 9 (i.e. such that a two-piece mould can be separated in a single direction). For example, the inlet passage is formed at an angle to the longitudinal axis, in the moulding direction, such that the outlet end 11b of inlet passage 11 extends to an outer surface of the insert and/or is in communication with the one or more recesses or open channels 10r in the mating surface 10m of the insert. In addition, the outlet 13 and the inlet end 11a of the inlet passage 11 are chamfered such that they can still be moulded at an angle, and various surfaces of the insert 10 include a draft angle for improved mouldability. The insert 10 may further comprise various set back surfaces, such as surface 10s shown in FIG. 5a, to improve the release and separation of the moulds from the insert 10.

A single direction moulding process may minimise the moulding cycle time and cost. Further, because the flow-resistant liquid passage 12 is formed by an interference fit between the insert 10 and the sidewall 50w of the drip chamber 50, the critical geometry and dimensions of the flow-resistant liquid passage 12, particularly the orifice 12b, can be achieved with regular injection moulding techniques and tolerances.

Although the insert 10 and device 100 is described above in the context of IV administration, it may also be used in series with other flow devices, such as electronic pumps and IV flow regulators to monitor and/or set a flow rate.

From reading the present disclosure, other variations and modifications will be apparent to the skilled person. Such variations and modifications may involve equivalent and other features which are already known in the art, and which may be used instead of, or in addition to, features already described herein.

Although the appended claims are directed to particular combinations of features, it should be understood that the scope of the disclosure of the present invention also includes any novel feature or any novel combination of features disclosed herein either explicitly or implicitly or any generalisation thereof, whether or not it relates to the same invention as presently claimed in any claim and whether or not it mitigates any or all of the same technical problems as does the present invention.

Features which are described in the context of separate embodiments may also be provided in combination in a single embodiment. Conversely, various features which are, for brevity, described in the context of a single embodiment, may also be provided separately or in any suitable sub-combination.

For the sake of completeness it is also stated that the term "comprising" does not exclude other elements or steps, the term "a" or "an" does not exclude a plurality, and any reference signs in the claims shall not be construed as limiting the scope of the claims.

The invention claimed is:

1. A flow metering insert for a drip chamber suitable for use in intravenous administration, the insert comprising:
   a primary liquid flow channel comprising:
      an inlet passage;
      an outlet; and
      a flow-resistant passage between the inlet passage and the outlet; and
   a flow indicating channel in communication with the primary liquid flow channel between the inlet passage and the flow-resistant passage;
   wherein the flow-resistant passage and the flow indicating channel is/are at least partially defined by one or more first recesses and/or open channels in a surface of the insert and, when the insert is inserted into a said drip chamber, the flow-resistant passage and the flow indicating channel are formed or located between the insert and a wall of the said drip chamber; and
   wherein the flow-resistant passage provides a resistance to a liquid flow through the primary liquid flow channel such that liquid is forced into the flow indicating channel and reaches a level or height in the flow indicating channel proportional to the rate of liquid flow through the primary liquid flow channel.

2. The insert of claim 1, wherein the surface is a mating surface of the insert configured to mate with, contact and/or seal against the wall of the said drip chamber when the insert is inserted into the said drip chamber.

3. The insert of claim 2, wherein the mating surface is configured to conform to the interior surface of the drip chamber when the insert is inserted into the drip chamber, and/or comprises one or more sealing ribs that extend around the one or more recesses or open channels to seal against the interior surface of the wall of the drip chamber when the insert is inserted into the drip chamber.

4. The insert of claim 1, wherein the flow-resistant passage is substantially U-shaped when the insert is arranged substantially vertically, such that, when inserted into the said drip chamber and arranged substantially vertically, liquid remains in the flow-resistant passage when a liquid flow is stopped.

5. The insert of claim 1, further comprising an exit chamber in communication with an outlet end of the flow-resistant passage and the outlet for directing a liquid flow from the flow-resistant passage to the outlet and, wherein the exit chamber comprises a second channel extending from the outlet end of the flow-resistant passage configured to direct a liquid flow from the flow-resistant passage to the outlet without forming drops; and wherein the second channel is or comprises a second open channel formed at least partially in a sidewall of the exit chamber and extending to a floor of the exit chamber; and wherein the second channel is configured to draw liquid into the exit chamber by capillary action.

6. The insert of claim 5, wherein the exit chamber comprises the outlet and wherein the outlet end of the flow-resistant passage is positioned at a level or height above a level or height of the outlet when the insert is arranged substantially vertically; and wherein the outlet is located in a floor of the exit chamber.

7. The insert of any of claim 6, wherein the exit chamber further comprises an overflow outlet positioned at a level or height between the level or height of the outlet and the level or height of the outlet end of the flow-resistant passage.

8. The insert of claim 1, wherein the flow indicating channel comprises a graduated scale to provide a visual measure of the liquid level or height in the flow indicating channel and thereby the rate of liquid flow through the primary liquid flow channel; and wherein the flow indicating channel comprises a visible float to facilitate reading of the liquid level.

9. The insert of claim 1, wherein the flow indicating channel comprises:

an inlet end in communication with an outlet end of the inlet passage and an inlet end of the flow-resistant passage, and the flow indicating channel extends substantially upwardly from its inlet end when the insert is arranged substantially vertically; and an open outlet end to permit an overflow; and/or a notch or opening in a wall of the flow indicating channel at a position above the inlet end configured to permit a liquid flow out of the flow indicating channel.

10. The insert of claim 9, wherein the flow indicating channel comprises a graduated scale to provide a visual measure of the liquid level or height in the flow indicating channel and thereby the rate of liquid flow through the primary liquid flow channel; and wherein the flow indicating channel comprises a visible float to facilitate reading of the liquid level; and wherein at least a portion of the flow indicating channel extends from its inlet end at an angle to the vertical when the insert is arranged substantially vertically to increase the graduation spacing on the scale; and wherein the flow indicating channel is curved about a longitudinal and/or a transverse axis of the insert.

11. The insert of claim 1, wherein the outlet comprises a drip-forming orifice.

12. The insert of claim 1, further comprising: a vent channel in communication with, and extending substantially upwardly from, an outlet end of the inlet passage configured for venting bubbles in a liquid flow exiting the inlet passage before entering the flow indicating channel; and/or one or more filter elements located at or near the inlet end of the inlet passage.

13. The insert of claim 2, shaped and/or configured to provide an interference fit within the said drip chamber wherein the seal between the mating surface and the interior surface of the wall of the said drip chamber is provided by the interference fit; and, the insert comprising one or more ribs or projections extending away from the insert and configured to contact a wall of the said drip chamber when the insert is inserted into the said drip chamber to provide the interference fit.

14. The insert of claim 1, wherein the insert is formed of or comprises a substantially rigid or deformable material;

and wherein the insert is or comprises a single piece moulding formed by an injection moulding process by a single direction injection moulding process.

15. A flow meter device comprising the insert of claim 1 and a flow chamber for receiving the insert, the flow chamber comprising:

an opening through which the insert can be inserted;

an outlet for receiving a liquid flow from the outlet of the insert; and one or more walls, at least one of the one or more walls including a substantially transparent portion for viewing the liquid level in the flow indicating channel.

16. The device of claim 15, further comprising a cover or lid connectable to the opening of the flow chamber, wherein the cover or lid comprises an inlet passage with an outlet end for connecting to the inlet passage of the insert and an inlet end for connecting to a liquid source; or wherein the flow chamber comprises an inlet passage with an outlet end for connecting to the inlet passage of the insert and an inlet end for connecting to a liquid source.

17. The device of claim 16, wherein the outlet end of the inlet passage of the cover/lid or flow chamber is connectable to the inlet passage of the insert by an interference fit; or wherein the outlet end of the inlet passage of the cover/lid or flow chamber is connectable to the inlet passage of the insert by a sealing element; and wherein the sealing element comprises a filter element for filtering a liquid flow upstream of the insert, and wherein the flow chamber is or comprises an at least partially transparent drip chamber for use in intravenous administration.

18. An intravenous administration set comprising:

an insert as defined in claim 1;

an at least partially transparent drip chamber for receiving the insert, the drip chamber comprising an outlet for receiving a liquid flow from the outlet of the insert;

tubing for connecting the outlet of the drip chamber to a point of administration; and a flow control device.

19. The intravenous administration set of claim 18, further comprising a cover or lid for the drip chamber, the cover or lid comprising an inlet passage with an outlet end for connecting to the inlet passage of the insert and an inlet end for connecting to a liquid source, or wherein the drip chamber comprises an inlet passage with an outlet end for connecting to the inlet passage of the insert and an inlet end for connecting to a liquid source; and wherein the outlet end of the inlet passage of the cover/lid or drip chamber is connectable to the inlet passage of the insert by an interference fit, and wherein the insert comprises a filter element located at or near the inlet end of the inlet passage of the insert; or wherein the outlet end of the inlet passage of the cover/lid or drip chamber is connectable to the inlet passage of the insert by a sealing element; and wherein the sealing element comprises a filter element for filtering a liquid flow upstream of the insert.

20. The insert of claim 3, wherein the flow resistant passage comprises an orifice; and wherein the orifice is located at or near a lower portion of the U-shaped flow-resistant passage when the insert is arranged substantially vertically.

* * * * *